(12) United States Patent
Son et al.

(10) Patent No.: US 9,803,909 B2
(45) Date of Patent: Oct. 31, 2017

(54) REFRIGERATOR

(71) Applicant: LG ELECTRONICS INC., Seoul (KR)

(72) Inventors: Mina Son, Changwon-si (KR);
Jeongyon Kim, Changwon-si (KR);
Hyeonjin Kim, Changwon-si (KR);
Byunghyun Kim, Changwon-si (KR);
Eunjeong Kim, Changwon-si (KR)

(73) Assignee: LG ELECTRONICS INC., Seoul (KR)

( * ) Notice: Subject to any disclaimer, the term of this patent is extended or adjusted under 35 U.S.C. 154(b) by 497 days.

(21) Appl. No.: 14/461,066

(22) Filed: Aug. 15, 2014

(65) Prior Publication Data

US 2014/0368103 A1 Dec. 18, 2014

Related U.S. Application Data

(62) Division of application No. 13/579,655, filed as application No. PCT/KR2011/007350 on Oct. 5, 2011.

(30) Foreign Application Priority Data

Dec. 29, 2010 (KR) ........................ 10-2010-0137690

(51) Int. Cl.
*F25D 17/04* (2006.01)
*F25D 23/02* (2006.01)
(Continued)

(52) U.S. Cl.
CPC ................ *F25D 17/04* (2013.01); *A61L 2/10* (2013.01); *B01D 46/00* (2013.01);
(Continued)

(58) Field of Classification Search
CPC .......... F25D 29/00; F25D 25/02; F25D 17/04; F25D 11/00; F25D 27/005;
(Continued)

(56) References Cited

U.S. PATENT DOCUMENTS 2,508,768 A * 5/1950 Munshower ............ F25D 17/06
62/414
3,702,544 A * 11/1972 Grinups .................. F25D 17/06
62/414

(Continued)

FOREIGN PATENT DOCUMENTS

EP         1 952 079     8/2008
JP         2000-180047 A     6/2000
(Continued)

OTHER PUBLICATIONS

U.S. Office Action dated Oct. 9, 2015 issued in U.S. Appl. No. 14/461,087.

(Continued)

*Primary Examiner* — Mohammad M Ali
(74) *Attorney, Agent, or Firm* — Ked & Associates LLP

(57) ABSTRACT

A refrigerator is disclosed. The refrigerator is able to store food at a low temperature and to effectively remove bacteria of the food stored in a storage room, to maintain the storage room clean.

48 Claims, 23 Drawing Sheets

(51) Int. Cl.

| | |
|---|---|
| *F25D 29/00* | (2006.01) |
| *A61L 2/10* | (2006.01) |
| *F21V 33/00* | (2006.01) |
| *F25D 11/00* | (2006.01) |
| *F25D 27/00* | (2006.01) |
| *B01D 46/00* | (2006.01) |
| *F25D 25/02* | (2006.01) |
| *G01G 19/52* | (2006.01) |
| *G01K 13/00* | (2006.01) |
| *G01N 33/48* | (2006.01) |
| *A61L 9/015* | (2006.01) |
| *A61L 9/14* | (2006.01) |
| *A61L 9/16* | (2006.01) |
| *A61L 9/20* | (2006.01) |
| *F21W 131/305* | (2006.01) |

(52) U.S. Cl.
CPC ......... *F21V 33/0044* (2013.01); *F25D 11/00* (2013.01); *F25D 17/042* (2013.01); *F25D 23/02* (2013.01); *F25D 25/02* (2013.01); *F25D 27/00* (2013.01); *F25D 27/005* (2013.01); *F25D 29/00* (2013.01); *G01G 19/52* (2013.01); *G01K 13/00* (2013.01); *G01N 33/48* (2013.01); *A61L 9/015* (2013.01); *A61L 9/14* (2013.01); *A61L 9/16* (2013.01); *A61L 9/205* (2013.01); *A61L 2209/111* (2013.01); *A61L 2209/14* (2013.01); *F21W 2131/305* (2013.01); *F25D 2317/041* (2013.01); *F25D 2317/0415* (2013.01); *F25D 2317/0417* (2013.01); *F25D 2317/067* (2013.01); *F25D 2400/361* (2013.01); *F25D 2700/06* (2013.01); *G01K 2207/04* (2013.01)

(58) Field of Classification Search
CPC ..... F25D 2317/0417; F25D 2317/0415; F25D 2700/06; F25D 23/02; F25D 27/00; F25D 17/042; F25D 2317/041; F25D 2400/361; F25D 2317/067; G01K 13/00; G01K 2207/04; G01G 19/52; G01N 33/48; A61L 9/14; A61L 9/205; A61L 9/015; A61L 9/16; A61L 2009/14; A61L 2209/111; F21W 2131/305
USPC ................... 62/331, 426; 312/401
See application file for complete search history.

(56) References Cited

U.S. PATENT DOCUMENTS

| | | | |
|---|---|---|---|
| 4,955,208 A | 9/1990 | Kawashima et al. | |
| 5,087,426 A | 2/1992 | Inoue et al. | |
| 5,901,564 A | 5/1999 | Comeau, II | |
| 6,526,767 B1* | 3/2003 | Lopes ................... | F25D 17/065 62/151 |
| 6,918,259 B2 | 7/2005 | Anderson et al. ................ | 62/78 |
| 7,137,677 B2* | 11/2006 | Hong ...................... | F25D 23/00 312/265.6 |
| 7,228,703 B2* | 6/2007 | Kim ..................... | F25D 17/065 62/353 |
| 7,284,390 B2* | 10/2007 | Van Meter ............. | F25C 5/005 62/344 |
| 7,600,388 B2* | 10/2009 | Vestal ................ | B01D 46/0086 55/DIG. 34 |
| 7,665,327 B2* | 2/2010 | Tunzi .................... | F25D 17/065 62/408 |
| 7,857,877 B2 | 12/2010 | Gunderson et al. ......... | 55/315.1 |
| 2002/0163436 A1 | 11/2002 | Singh | |
| 2004/0107726 A1 | 6/2004 | Kim et al. ..................... | 62/441 |
| 2005/0011171 A1 | 1/2005 | Lee et al. ....................... | 55/471 |
| 2005/0284158 A1 | 12/2005 | Lee et al. ....................... | 62/126 |
| 2006/0130498 A1 | 6/2006 | Joshi | |
| 2006/0213904 A1 | 9/2006 | Kates | |
| 2007/0107452 A1 | 5/2007 | Kim et al. | |
| 2007/0157646 A1* | 7/2007 | Kim ....................... | F25D 17/042 62/187 |
| 2007/0180839 A1 | 8/2007 | Kim ................................ | 62/178 |
| 2008/0016898 A1 | 1/2008 | Vestal | |
| 2008/0168790 A1 | 7/2008 | Hurlebaus et al. ............. | 62/331 |
| 2008/0245079 A1* | 10/2008 | Lim ........................ | F25D 23/12 62/66 |
| 2008/0307818 A1 | 12/2008 | Min | |
| 2009/0052161 A1* | 2/2009 | Lee ......................... | F25D 27/00 362/94 |
| 2009/0217694 A1 | 9/2009 | Kim et al. ...................... | 62/426 |
| 2009/0271243 A1 | 10/2009 | Sholl | |
| 2009/0282853 A1 | 11/2009 | Lee et al. ........................ | 62/317 |
| 2009/0309960 A1 | 12/2009 | Park | |
| 2010/0170278 A1 | 7/2010 | Min | |

FOREIGN PATENT DOCUMENTS

| | | |
|---|---|---|
| JP | 2004-020113 A | 1/2004 |
| JP | 2005-76980 | 3/2005 |
| JP | 2005-195203 | 7/2005 |
| JP | 2006-300351 | 11/2006 |
| JP | 2008-207151 | 9/2008 |
| JP | 2008-275243 | 11/2008 |
| JP | 2009-030919 | 2/2009 |
| JP | 2009-047382 | 3/2009 |
| JP | 2009-516820 | 4/2009 |
| JP | 2009-125697 | 6/2009 |
| KR | 1997-0014828 | 4/1997 |
| KR | 10-2007-0052507 | 5/2007 |
| WO | WO 2007/061238 | 5/2007 |

OTHER PUBLICATIONS

U.S. Appl. No. 14/461,087, filed Aug. 15, 2014.
U.S. Office Action issued in U.S. Appl. No. 13/579,655 dated Jan. 25, 2016.
European Search Report dated Oct. 14, 2016.
International Search Report and Written Opinion dated Apr. 27, 2012.
Chinese Office Action dated Jan. 24, 2014, issued in Application No. 201180007836.9 (with English translation).
Office Action dated Aug. 14, 2014, issued in U.S. Appl. No. 13/579,655.
European Search Report dated Mar. 31, 2017 issued in Application Serial No. 11852667.2.
U.S. Office Action dated Jun. 14, 2016 issued in U.S. Appl. No. 14/461,087.
U.S. Office Action dated Jun. 22, 2016 issued in U.S. Appl. No. 13/579,655.
U.S. Appl. No. 13/579,655, filed Aug. 17, 2012.

* cited by examiner (a)

(b)

(a)

(b)

(a)

(b)

(a)

(b)

(a)

(b)

REFRIGERATOR

CROSS-REFERENCE TO RELATED APPLICATION(S)

This application is a Divisional application of prior co-pending U.S. patent application Ser. No. 13/579,655 filed Aug. 17, 2012, which is a U.S National Stage application under 35 U.S.C. §371 of PCT Application No. PCT/KR2011/007350, filed Oct. 5, 2011, which claims priority to Korean Patent Application No. 10-2010-0137690, filed Dec. 29, 2010, whose entire disclosures are hereby incorporated by reference.

BACKGROUND

1. Technical Field

The present invention relates to a refrigerator that is able to store food at a low point of temperature and to remove bacteria of the food stored in a storage room effectively, to maintain the storage room clean.

2. Background Art

Generally, a refrigerator is an electric appliance that can store food at a low temperature to preserve food fresh for a relatively long time. Based on statuses of stored items, which are the food, cold air is controlled to preserve them frozen or refrigerated.

The cold air supplied to the inside of the refrigerator is generated by heat exchange of refrigerant, and it is constantly supplied to the inside of the refrigerator while a cycle configured of compression, condensation, expansion and evaporation is performed repeatedly. The supplied refrigerant is uniformly transported into the refrigerator by convection, such that the food located in the refrigerator may be preserved at a desired temperature.

Such a refrigerator may be categorized, based on a structure of freezer and refrigerator compartments provided therein, into a traditional top freezer type refrigerator, a side by side refrigerator, and a bottom freezer type refrigerator.

The traditional top freezer type refrigerator includes a refrigerator compartment located on a top thereof and a refrigerator compartment located at a bottom thereof. The side by side type refrigerator includes freezer and refrigerator compartments located side by side.

The bottom freezer type refrigerators have been used a lot in North America and Europe. Such a bottom freezer type refrigerator includes a large-sized refrigerator compartment located on a top and a freezer compartment smaller than the refrigerator compartment located at a bottom. Such a refrigerator includes a case having at least one storage room formed therein and a door rotatably coupled to the case to selectively open and close the storage room.

The storage room of the refrigerator is typically partitioned into freezer and refrigerator compartments. Behind the storage room may be arranged an evaporator for generating cold air by heat-exchanging with air inside the storage room and a fan for blowing the air inside the storage room into the evaporator and for re-storing the heat-exchanged cold air into the storage room.

Moreover, a variety of functions for user convenience may be provided. To realize such functions, a home bar may be provided in the door or a plurality of baskets may be provided in a rear surface of the door, to store or keep a proper amount of food or food containers in the door.

In such a refrigerator vegetables and fruits, fish, various food materials and cooked-food may be stored. Unless the storage room is cleaned periodically, the refrigerator might be full of unpleasant smells generated from the variety of food stored in the storage room, and bacteria and viruses might reproduce. Because of this, sanitation could be poor and the user might have an unpleasant feeling.

Also, bacteria and the like might spread into the other food or move inside the refrigerator along the cold air circulation. Because of this, sanitation inside the refrigerator might be poor.

DISCLOSURE OF INVENTION

Technical Problem

To solve these problems, an object of the present invention is to provide a refrigerator that is able to remove bacteria from food stored in a storage room and from air inside the storage room effectively and to maintain the storage room clean.

Another object of the present invention is to provide a refrigerator that is able to maintain clean a plurality of storage rooms via an auxiliary sterilization passage independent from a cold air passage.

A further object of the present invention is to provide a refrigerator that is able to automatically sterilize/deodorize the storage room and decompose remnants of dead bacteria.

A still further object of the present invention is to provide a refrigerator that is able to remove allergens located in the storage room to manage the storage room sanitarily and to keep freshness of the stored food.

A still further object of the present invention is to provide a refrigerator that is able to selectively perform sterilization based on introduction of food, change of internal temperature, or usage of the food to reduce power consumption.

A still further object of the present invention is to provide a refrigerator that is able to detect a kind and amount of bacteria or odor factors located in the storage room to display the detected information to the user.

A still further object of the present invention is to provide a refrigerator that is able to recognize image information relating to an appearance of a specific food or distribution of temperatures to acquire freshness of the food and to display the freshness to the user.

Technical Solution

To achieve these objects and other advantages and in accordance with the purpose of the invention, as embodied and broadly described herein, a refrigerator includes a cabinet comprising at least one storage room provided therein for low temperature storage; a compressor provided in the cabinet, to compress refrigerant; at least one door to open and close the storage room selectively; a filter module comprising a housing arranged in the storage room, with an air inlet and an air outlet formed therein, a plurality of sterilization filters arranged in the housing and a fan; and a control unit to control the operation of the filter module.

The housing may include a front housing having the air inlet formed therein; a rear housing coupled to the front housing, having the air outlet formed therein to arrange the fan; and a front panel arranged in a front of the front housing.

The plurality of the sterilization filters may be configured of first to third sterilization filters arranged along the air outlet from the air inlet sequentially, and the size of mesh may be getting smaller from the first sterilization filter to the third sterilization filter. The third sterilization filter may have a zebra pattern. Leuconostoc enzyme may be coated on at least one of the sterilization filters. A protein activity inhibitor may be further coated on the at least one of the sterilization filters.

The filter module may further include a deodorization filter to deodorize the air having passed through the sterilization filters. The filter module may further include an anti-allergen filter. The anti-allergen filter may include at least one selected from a group composed of activated carbon (charcoal), silver (Au), allercatcher fiber, co-phthalocyanine and Fe-phthalocyanine. The activated carbon may be T-SCOB, T-E or T-TS impregnated charcoal.

The cabinet may include an inner case having the storage room provided therein and an outer case defining an exterior appearance of the refrigerator, a cold air duct arranged in a space between the front case and the rear plate to supply cold air to the storage room, and a filter duct comprising a plurality of outlets to draw the sterilized air exhausted from the filter module therein and to transport the drawn sterilized air to the storage room. A passing hole may be provided in the inner case, corresponding to the outlets of the filter duct, and the sterilized air may be drawn into the inner case via the passing hole.

The inner case may be partitioned into a plurality of storage sections, and at least one passing hole may be provided in each of the storage sections. The cold duct and the filter duct may be connected with each other partially, and cold air and sterilized air may be supplied to the storage room together.

The control unit may drive the filter module for a preset time period, when a preset integrated time of the compressor passes. The control unit may drive the filter module for a first time period and stop the filter module for a second time period, and the control unit may repeat the driving and stopping of the filter module multiple times. The integrated time of the compressor may be 5 hours and the first time period may be 10 minutes and the second time period may be 5 minutes.

The control unit may drive the filter module for a preset time period when the door is closed based on opening and closing of the door. The control unit may drive the filter module for a preset time period when the door is closed based on at least one of a frequency of door opening/closing and a door opening time. The control unit may stop the driving of the filter module when the door is opened during the driving of the filter module. The control unit may stop the driving of the filter module when a defrost operation starts during the driving of the filter module.

In another aspect of the present invention, a refrigerator includes a cabinet comprising at least one storage room provided therein for low temperature storage; a compressor provided in the cabinet, to compress refrigerant; at least one door to selectively open and close the storage room; a filter module comprising at least one UV lighting source to irradiate an ultraviolet light toward air inside the storage room and a photocatalyst filter to filter the air having the UV light irradiated thereto; and a control unit to control the operation of the filter module. Titanium may be coated on the photocatalyst filter.

The filter module may include a housing arranged in the storage room, with an air inlet and an air outlet formed therein, and a fan arranged adjacent to the air outlet of the housing, and the UV lighting source may be arranged adjacent to the air inlet within the housing and the photocatalyst filter may be arranged adjacent to the air outlet within the housing.

The cabinet may include an inner case having the storage room provided therein and an outer case defining an exterior appearance of the refrigerator, a cold air duct arranged in a space between the front case and the rear plate to supply cold air to the storage room, and a filter duct comprising a plurality of outlets to draw the sterilized air exhausted from the filter module therein and to transport the drawn sterilized air to the storage room. A passing hole may be provided in the inner case, corresponding to the outlets of the filter duct, and the sterilized air may be drawn into the inner case via the passing hole. The inner case may be partitioned into a plurality of storage sections, and at least one passing hole may be provided in each of the storage sections.

The UV lighting source may be operated based on at least one of a light emission duration time, a light emission intensity, and a light emission period that are memorized in the control unit. The UV lighting source may be operated based on at least one of a door opening status and a temperature change of the storage room.

The filter module may further include an anti-allergen filter. The anti-allergen filter may include at least one selected from a group composed of activated carbon (charcoal), silver (Au), allercatcher fiber, co-phthalocyanine and Fe-phthalocyanine.

In a further aspect of the present invention, a refrigerator includes a cabinet comprising an inner case having the storage room provided therein and an outer case defining an exterior appearance thereof; a sensor unit to detect a contamination source inside the storage room; at least one door to selectively open and close the storage room; a filter duct arranged between the front case and the rear plate, to flow air inside the inner case therein; a filter module provided in the filter duct, the filter module comprising a steam generation unit to spray high-temperature steam toward the air drawn into the filter duct and a fan to adjust air flow inside the filter duct; and a control unit to control the operation of the filter module based on the result of the detection performed by the sensor unit.

The sensor unit may include at least one of a bio-sensor to detect a specific bacteria contaminant and a gas sensor to detect an offensive smell factor. The sensor unit may include a camera unit arranged in the storage room, to detect and visualize an image of a stored food, and the control unit may determine spoiling of the stored food based on a difference between an image of the stored food pre-memorized therein and the image of the stored food detected by the camera unit.

The refrigerator may further include a display part provided in a door, to image surface temperature distribution of the stored food visualized by the camera unit and to display the imaged surface temperature distribution to the user. The display part may display the spoiling of the stored food determined by the control unit to the user. The camera unit may detect at least one of a temperature, a color, and a shape of the stored food. The control unit may increase cooling load of the storage room for a preset time period after steam spraying is complete.

The refrigerator may further include a display part to display a contamination status of the storage room detected by the sensor unit to the user. The sensor unit may include a weight sensor to recognize weight change of the stored food.

Advantageous Effects

As mentioned above, according to the refrigerator relating to at least one embodiment, the food stored in the storage room and air inside the storage room may be sterilized effectively. Also, the storage room may be maintained clean.

Further, according to the refrigerator relating to at least one embodiment, the plurality of the storage rooms may be maintained clean by the sterilization passage independently separated from the cold air passage.

Still further, according to the refrigerator relating to at least one embodiment, the storage room may be sterilized and deodorized. In addition, remains of dead bacteria may be self-discomposed.

Still further according to the refrigerator relating to at least one embodiment, allergens that are allergy generation factors may be removed from the inside of the storage room. Because of this, the storage room may be managed more sanitarily and freshness of the stored food may be kept.

Still further, according to the refrigerator relating to at least one embodiment, the sterilization may be selectively performed based on food introduction, internal temperature change, or usage. Because of this, power consumption may be reduced.

Still further, according to the refrigerator relating to at least one embodiment, kinds and an amount or a smell factor of bacteria located in the storage room may be detected and the detected information may be displayed to the user.

Still further, according to the refrigerator relating to at least one embodiment, image information relating to a shape or temperature distribution of specific food may be acquired and freshness of the food may be figured out, to display the freshness of the food to the user.

BRIEF DESCRIPTION OF THE DRAWINGS

The accompanying drawings, which are included to provide further understanding of the disclosure and are incorporated in and constitute a part of this application, illustrate embodiments of the disclosure and together with the description serve to explain the principle of the disclosure and in the drawings.

BEST MODE

Figure 1:
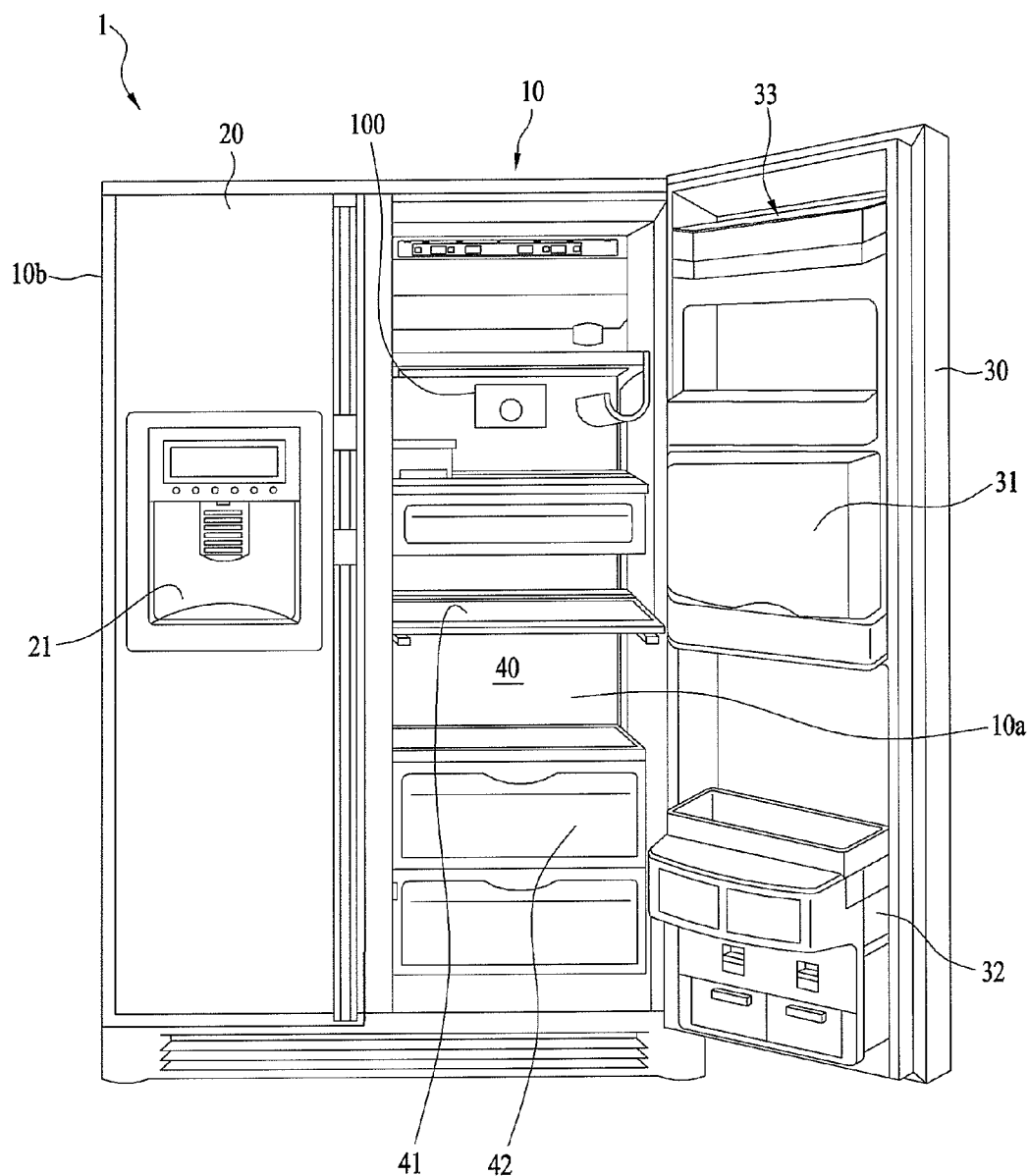
FIG. 1 is a perspective view illustrating a door of a refrigerator according to an embodiment, which is partially open.

As follows, a refrigerator according to an exemplary embodiment of the present invention will be described in detail in reference to the accompanying drawings. The accompanying drawings illustrate examples of the present invention and they are provided to explain the present invention in more detail. However, the scope of the present invention is not limited by the drawings.

Regardless of numeral references, the same reference numbers will be used throughout the drawings to refer to the same or like parts and repeated description will be omitted. The size and appearance of each element shown in the drawings may be exaggerated or shrunk.

In the meanwhile, the terms including ordinal numbers such as 'first' and 'second' used in the specification may be used to explain a variety of elements and the elements are not limited by the terms. The terms are used only for distinguishing one of the elements from the other.

Figure 2:
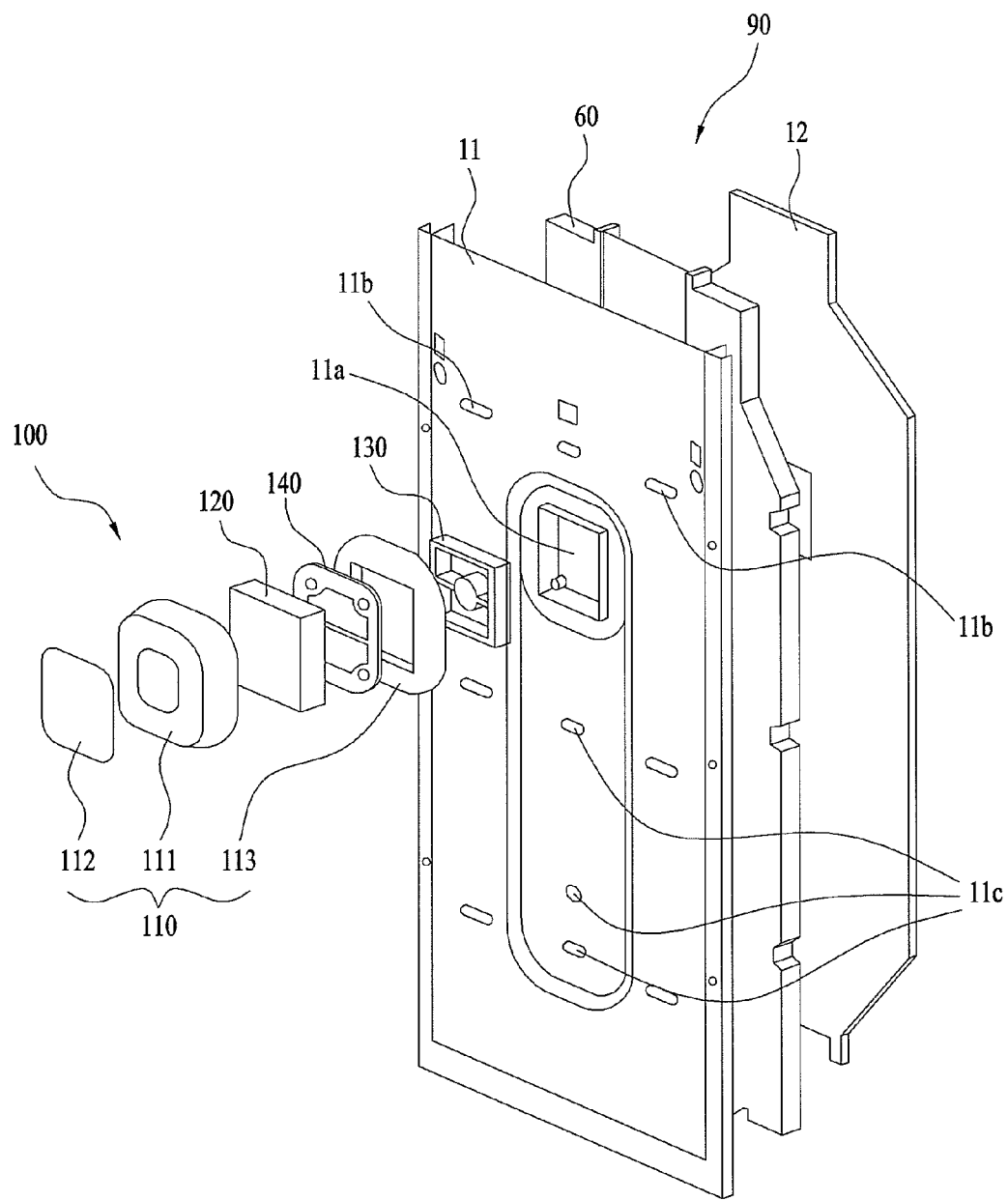
FIG. 2 is a perspective view illustrating key parts of a refrigerator according to an embodiment.

FIG. 1 is a perspective view illustrating a door of a refrigerator according to an embodiment of the present invention, which is partially open. FIG. 2 is a perspective view illustrating key parts of a refrigerator according to an embodiment of the present invention.

The refrigerator 1 according to the embodiment of the present invention may be applicable to various types of refrigerators, for example, a traditional top freezer type refrigerator, a side by side type refrigerator, or a bottom freezer type refrigerator. More specifically, the refrigerator may be a refrigerator including a cabinet 10 having at least one storage room formed therein for low temperature storage and at least one door 20 and 30 rotatably coupled to the cabinet 10 to selectively open and close the storage room.

As follows, the side by side type refrigerator widely used in recent years will be embodied which includes freezer and refrigerator compartments located side by side, being selectively closed by doors provided respectively, for explanation convenience.

The refrigerator 1 may include a cabinet 10 having at least one storage room for low temperature storage, a compressor (not shown) provided in the cabinet 10 to compress refrigerant, at least one door 20 and 30 rotatably coupled to the cabinet 10 to open and close the storage room, a filter module 100 mounted in the storage room of the cabinet 10, and a control unit (not shown) configured to control operation of the filter module 100.

With reference to FIGS. 1 and 2, the refrigerator 1 according to this embodiment may include the cabinet 10 capable of providing a room in which food and food containers may be stored at a relatively low temperature and an exterior appearance of the refrigerator. The cabinet 10 may have an approximately cube shape, with an open front to receive food and food containers therethrough.

The cabinet 10 of the refrigerator 1 may include an outer case 10b and at least one inner case 10a capable of providing a storage room to freeze or refrigerate food. With reference to FIG. 2, a cold air duct 60 may be arranged between the front plate 11 and the rear plate 12 to supply cold air to the inside of the storage room 40.

The at least one door 20 and 30 may be rotatably coupled to the open front of the cabinet 10 to selectively open and close the open front of the cabinet 10. FIG. 1 illustrates a side by side type refrigerator which includes a first door 20 and a second door 30 coupled to the cabinet 10 to open and close a left storage room (50, see FIG. 7) and a right storage room 40, respectively.

Various functions may be added to the refrigerator 1 to allow a user to use the refrigerator 1 conveniently. To realize such functions, a dispenser 21 and a home bar 31 may be further provided in the doors 20 and 30. The user may keep and store a predetermined amount of food or food containers in the home bar 31, and he or she may dispense purified water or ice from the dispenser 21.

At least one basket 33 may be arranged in a rear surface of the door 30.

Also, in case of the side by side type refrigerator 10, an internal space of the cabinet 10 may be partitioned into a left room and a right room. Commonly, the left room is employed as a freezer compartment (50, see FIG. 7) storing food and food containers at below zero temperatures and the right room is employed as a refrigerator compartment 40 storing food and food containers at above zero temperatures.

The freezer compartment 50 may freeze the food stored therein below the zero temperatures, and it is used to store the food for a relatively long time period. The refrigerator compartment 40 maintains the temperature lower than room temperature and it is used to store the food fresh.

A plurality of shelves 51 and 41 may be provided in the freezer compartment (50, see FIG. 7) and the refrigerator compartment 40. The food and the food containers may be placed on the plurality of the shelves 51 and 41. Because of the shelves 51 and 41, internal rooms of the freezer and refrigerator compartments may be partitioned into a plurality of layered spaces. Also, at least one drawer 52 and 42 may be further provided in the freezer compartment (50, see FIG. 7) and the refrigerator compartment 40 to receive food, such as fruit or vegetables.

The refrigerator 1 may stored fruit and vegetables, meats, fish, a variety of food materials and related cooking materials. The plurality of the storage spaces may be formed in the cabinet 10 by the shelves and drawers. Because of this, separate storage for each kind of food may be possible.

For example, a single drawer 42 of the drawers provided in the refrigerator compartment 40 may be used as a storage space for fruit and/or vegetables. Another drawer may be used as a storage space for meats or fish. The other drawer 32 provided in the rear surface of the door 30 may be used as storage space for grains, such as rice, beans, or adzuki beans.

Figure 3:
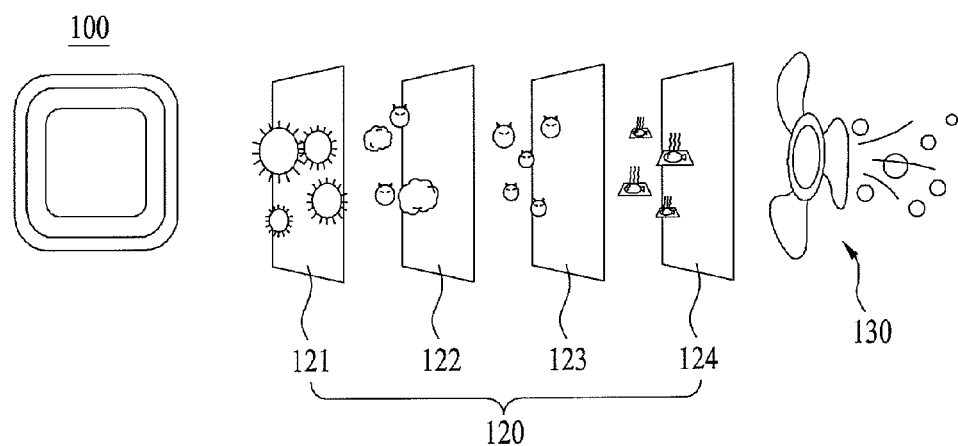
FIG. 3 is a conceptual diagram illustrating an example of an operation status of a filter module of a refrigerator according to an embodiment.
Figure 4:
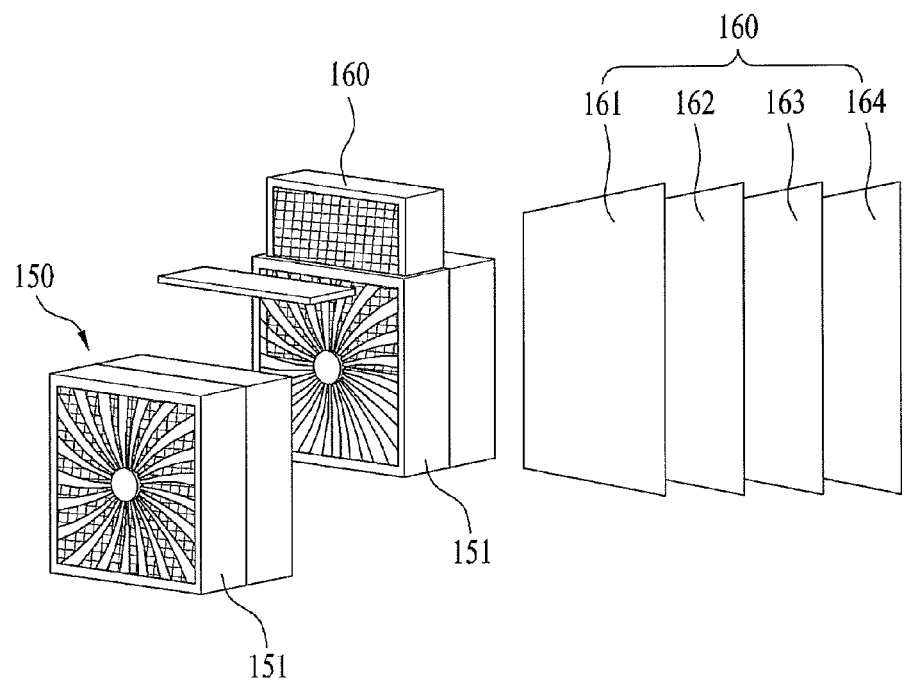
FIG. 4 is a conceptual diagram illustrating another example of an operation status of a filter module of a refrigerator according to an embodiment.
Figure 5:
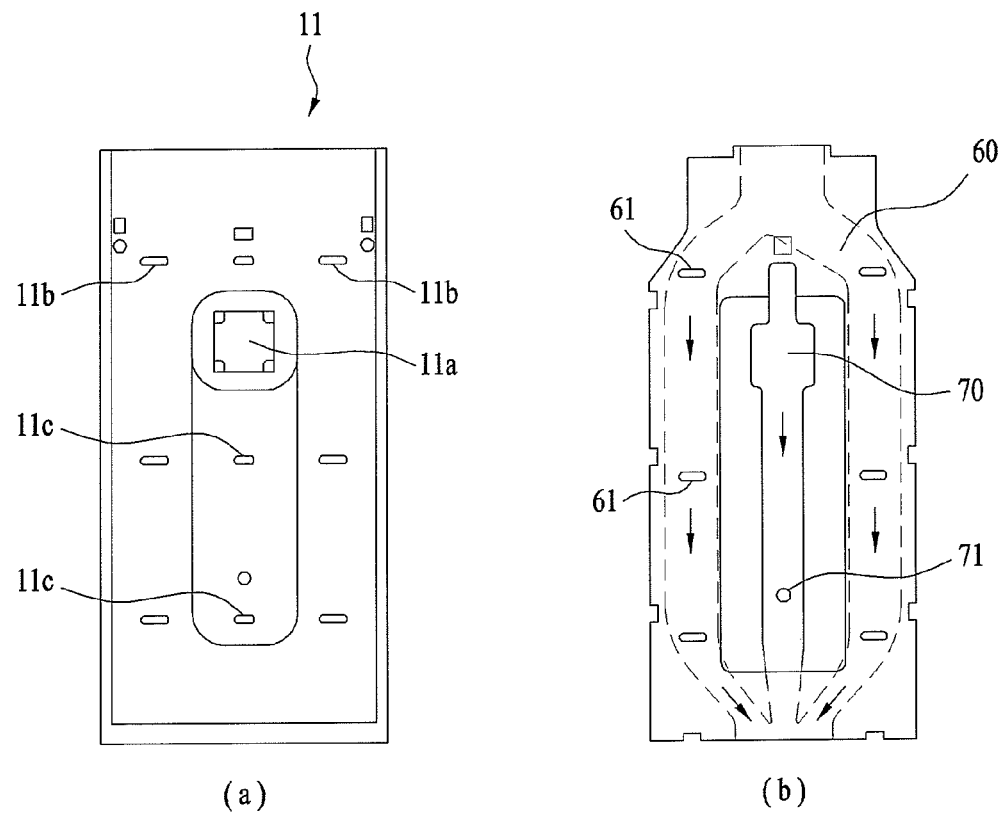
FIGS. 5A-5B are front views illustrating key parts of a refrigerator according to an embodiment.

FIG. 3 is a conceptual diagram illustrating an example of an operation status of a filter module of a refrigerator according to an embodiment. FIG. 4 is a conceptual diagram illustrating another example of an operation status of a filter module of a refrigerator according to an embodiment. FIGS. 5A-5B are front views illustrating key parts of a refrigerator according to an embodiment.

Figure 6A:
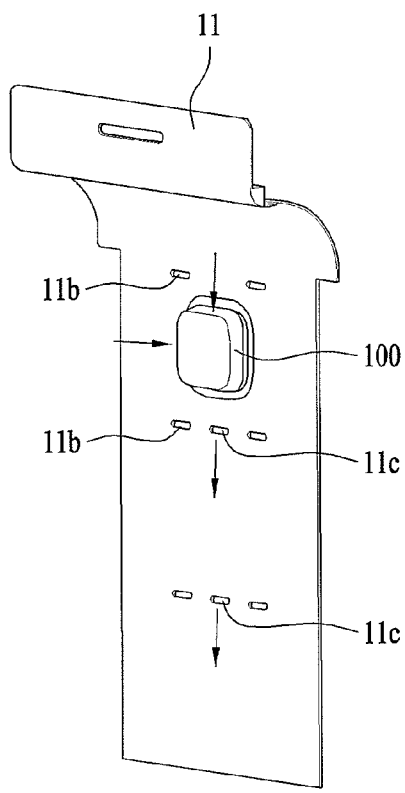
FIGS. 6A-6B and 7 are conceptual diagrams illustrating a multi duct of a refrigerator according to an embodiment.
Figure 6B:
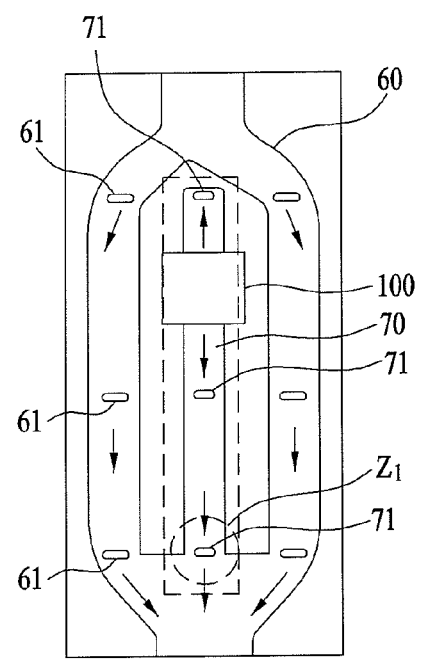
Figure 7:
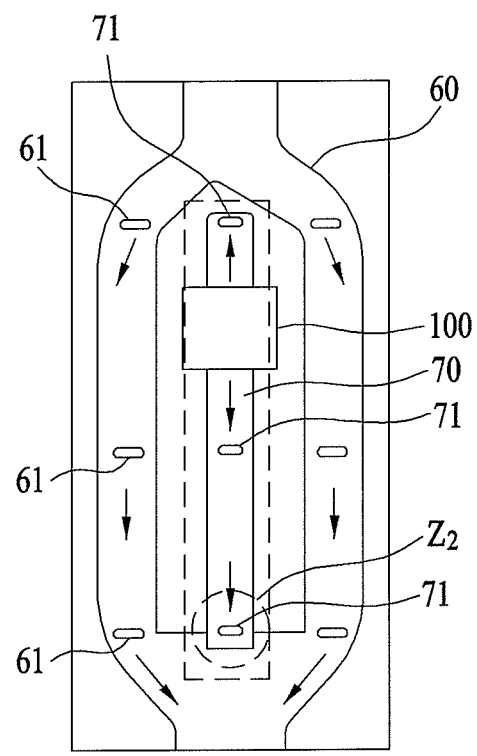
Figure 8:
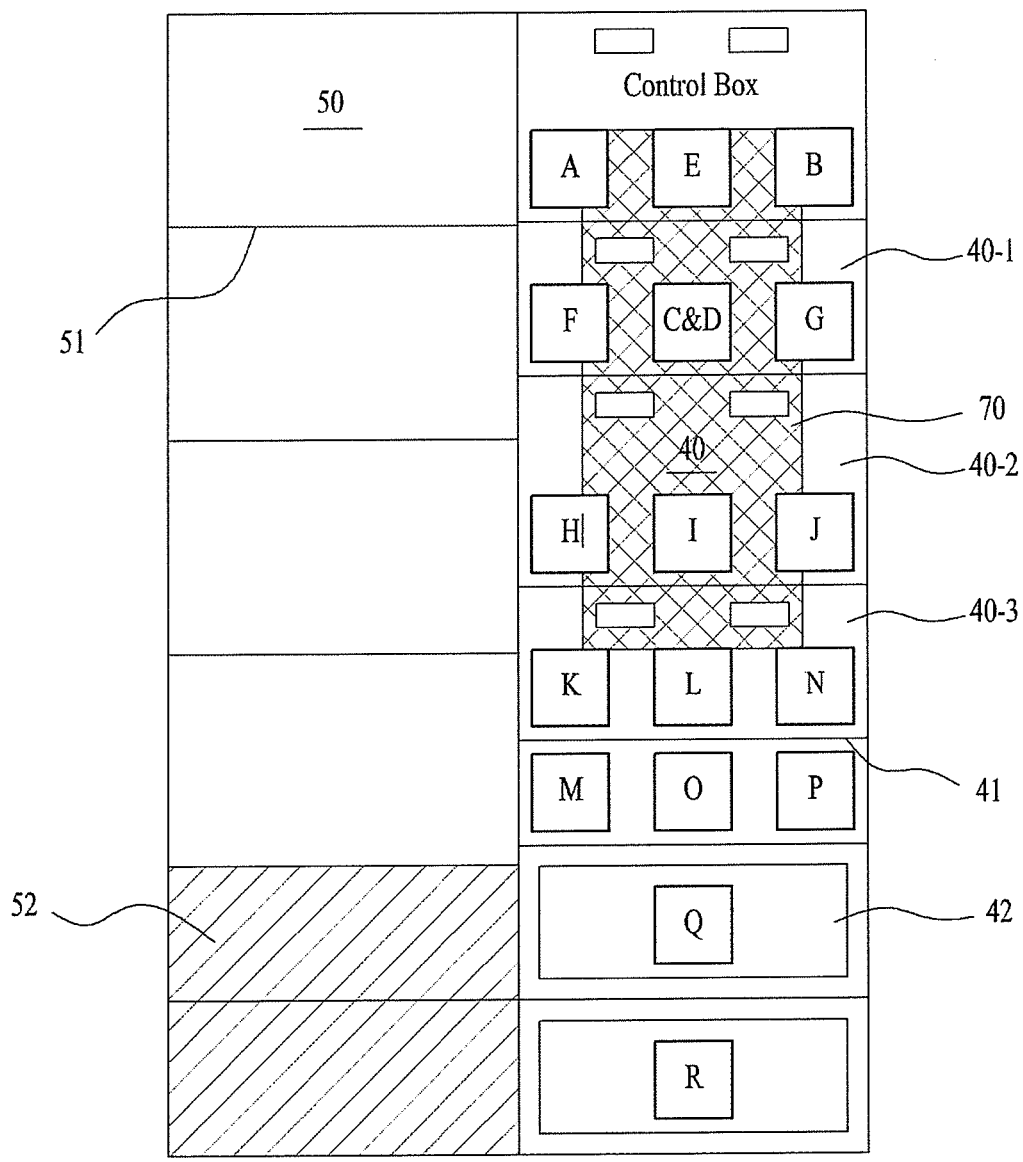
FIGS. 8 and 9A-9B are conceptual diagrams illustrating an example of an operation status of a filter module and a multi duct.
Figure 9:
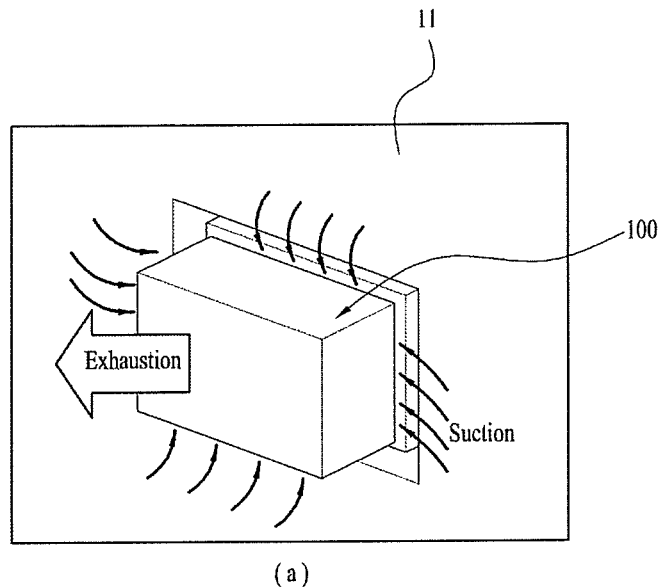
Figure 9:
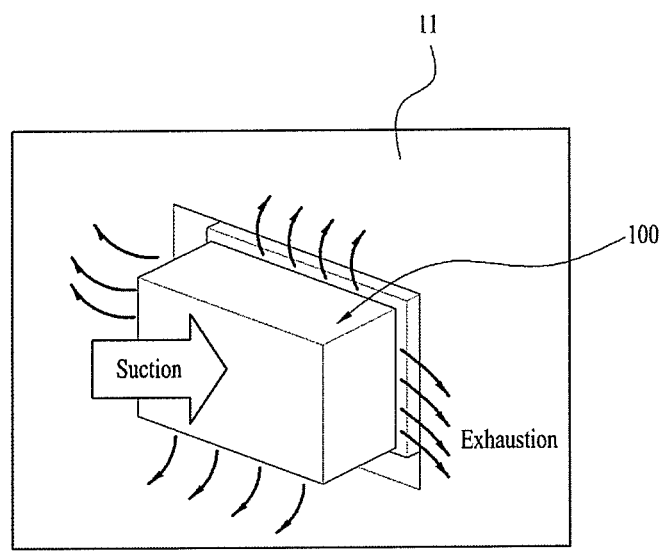

Also, FIGS. 6A-6B and 7 are conceptual diagrams illustrating a multi duct of a refrigerator according to an embodiment. FIGS. 8 and 9A-9B are conceptual diagrams illustrating an example of an operation status of a filter module and a multi duct.

The filter module 100 may include a housing 110 having an air inlet (not shown) and an air outlet (not shown), a plurality of sterilization filters 120 arranged in the housing 110, and a fan 130 for sucking air inside the storage space into the filter module 100 and for exhausting the sterilized air outside of the housing 110. The housing 110 may have various appearances and structures. According to one example in reference to FIG. 2, the housing 100 may include a front housing 111 having the air inlet formed therein, a rear housing 113 having the air outlet formed therein and coupled to a rear side of the front housing 111 to arrange the fan 130 therein, and a front panel 112 coupled to a front of the front housing 111.

With such a structure, air inside the storage room 40 may be sucked via a gap formed between the front panel 112 and the front housing 111. The sucked air may reach the sterilization filter 120 via the air inlet formed in the front housing 111. In addition, the sterilization filter 120 may be detachably arranged in the housing, with a replaceable structure. Also, a slit plate 140 may be arranged in the filter module 110 to guide air flow between the sterilization filters 120 and the fan 130.

With reference to FIG. 3, the sterilization filters 120 may be composed of a first sterilization filter 121, a second sterilization filter 122, and a third sterilization filter 123 that are sequentially arranged from the air inlet toward the air outlet of the housing 110. The first to third sterilization filters 121, 122 and 123 may perform three steps of sterilization.

A size of mesh may get smaller from the first sterilization filter 121 toward the third sterilization filter 123. For example, the first sterilization filter 121 may have a mesh with a size of approximately 100 μm or more. The second sterilization filter 122 may have a mesh with a size of approximately 5 μm or more, and the third sterilization filter 123 may have a mesh with a size of approximately 2.5 μm.

In addition, the filter module 100 may include a deodorization filter 124 used to deodorize the air having passed the sterilization filters 121 to 123.

The filter module 100 having the structure mentioned above may keep the air inside the storage room 40 clean using three steps of sterilization and a single step of deodorization.

Leuconostoc enzymes may be coated on at least one of the sterilization filters 121 to 124. The leuconostoc enzyme is a kind of Kimchi's lactic enzyme and it is highly effective in sterilization. Also, a protein activity inhibitor may be additionally coated on the sterilization filters 121 to 124, and the sterilization filters 121 to 124 may include an organic/inorganic binder and water. Preferably, a compound of Kimchi's lactic enzyme extract and protein activity inhibitor may be coated on the sterilization filters 121 to 124.

The third sterilization filter 123 may have a zebra pattern (not shown) to increase a coating area of the enzymes. The filter module 100 may further include an anti-allergen filter.

In reference to FIG. 4, a filter module 150 shown in FIG. 4 may include a housing 151 having an air inlet and an air outlet formed therein, a filter box 160 detachably held in the 151, and a fan (not shown) arranged in the housing 151. The filter module 150 shown in FIG. 4 may be integrally formed with the housing, which is a different characteristic, in comparison with the filter module 100 mentioned above. Also, the filter box 160 may include a plurality of sterilization filters 161 and 162, an anti-allergen filter 163, and a deodorization filter 164, which are the same as mentioned above.

The anti-allergen filter 163 may include at least one selected from a group composed of activated carbon (charcoal), silver (Au), allercatcher fiber, co-phthalocyanine, and Fe-phthalocyanine. The activated carbon may be T-SCOB impregnated charcoal having encapsulated silver, T-E impregnated charcoal to selectively soak ethylene or T-TS impregnated charcoal to selectively soak aldehyde that is generated from Doenjang or fermented foods. Such an anti-allergen filter 163 may perform a function of removing allergens located in the storage room 40.

An object of the embodiments may be to provide a refrigerator that is able to maintain the plurality of the storage rooms via the auxiliary sterilization passage independent from the cold air passage. With reference to FIGS. 2 and 5 to 7, in the cabinet 10 may be arranged the cold air duct 60 configured to supply cold air to the storage room 40, located in a predetermined space formed between the front plate 11 and the rear plate 12, and a filter duct 70 that draws the sterilized air from the filter module 100 therein, with a plurality of outlets 71 to transport the drawn sterilized-air to the storage room 40. The multi duct 90 may include the cold air duct 60 and the filter duct 70.

With reference to FIGS. 5A-5B, an opening 11a may be formed in the front plate 11 to arrange the filter module 100 therein, and a cold air supply hole 11b may be formed in the front plate 11 to supply cold air to the storage room. Also, a passing hole 11c may be provided in the inner case to supply the sterilized-air to the storage room via the filter duct 70 (second duct). The passing hole 11c may be located at a position corresponding to the outlet 71 of the filter duct 70 (second duct), and sterilized air may be drawn into the front plate 11 via the passing hole 11c.

More specifically, the air drawn into the filter module 100 from the storage room via the air inlet of the housing may be sterilized and deodorized while passing through the sterilization filters and the deodorization filter. The sterilized air may be drawn into the multi-duct 70 along the opening 11a of the inner case, after passing through the air outlet of the housing 110. Hence, the sterilized air flowing inside the filter duct 70 (second duct) passes through the outlet 71 of the filter duct 70 (second duct) and the passing hole 11c of the front plate 11, sequentially, to be supplied to the storage room.

The cold air duct 60 may be formed to surround the filter duct 70 (second duct) to make better use of a space formed between the inner case and the rear plate 12. Also, with reference to FIG. 6B, a longitudinal end (Z1) of the filter duct 70 (second duct) may be connected with the cold air duct 60, to draw the sterilized air into the front plate 11 together with the cold air. With reference to FIG. 7, a longitudinal end (Z2) of the filter duct 70 (second duct) may be separated from the cold air duct 60, to draw the sterilized air into the inner case separate from the cold air.

With reference to FIG. 8, inner spaces 40 and 50 of the front plate 11 may be partitioned into a plurality of storage sections 40-1 to 40-3 by the shelves 41 and 51. The filter module 100 may be arranged in a specific area (A to R) of each storage section. As mentioned above, when the filter module 100 is arranged in a specific area of one of the storage sections (for example, 40-2), the sterilized air may be supplied to storage sections 40-1 and 40-3 via the filter duct 70 (second duct) mentioned above. Also, at least one outlet 71 of the filter duct 70 (second duct) and at least one passing hole 11c of the front plate 11 may be provided in each of the storage sections 40-1 to 40-3.

With reference to FIG. 6B, the cold air duct 60 and the filter duct 70 (second duct) may be connected with each other at some area (Z1). With this structure, the cold air and the sterilized air may be supplied to the storage room together.

So far, it is described that the sterilized air exhausted from the filter module 100 may be supplied to neighboring storage sections (40-1 to 40-3) via the filter duct 70 (second duct). However, different from this, with reference to FIGS. 9A-9B, an air path may be formed in a front surface or a side surface of the filter module and the sterilized air may be then circulated into the storage sections directly, not via the filter duct 70 (second duct).

It is shown in FIGS. 9A-9B that the sterilized air may be exhausted via a front surface of the filter unit 100, with air inside the storage sections being drawn into the filter unit 100 via at least one side surface of the filter unit 100. Also, it is shown that the sterilized air is exhausted via at least one side surface of the filter unit 100, with the air inside the storage room being drawn via the front surface of the filter unit 100. However, the present invention is not limited thereby and the filter unit 100 may be arranged, spaced apart a proper distance from an inner circumferential surface of the inner case.

According to an example, the air inside the storage may be drawn via the front surface of the filter unit 100, and the sterilized air may be exhausted via the space between the filter unit 100 and the front plate 11.

Figure 10:
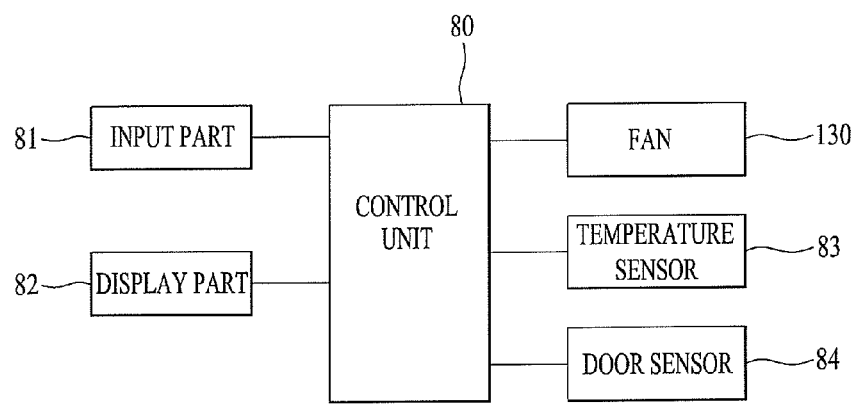
FIG. 10 is a block view of a refrigerator according to an embodiment.
Figure 11:
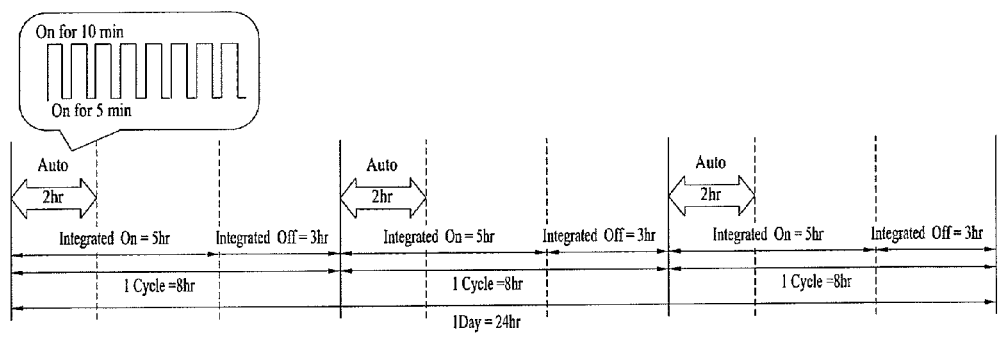
FIG. 11 is a diagram illustrating a control method of a refrigerator according to an embodiment.
Figure 14:
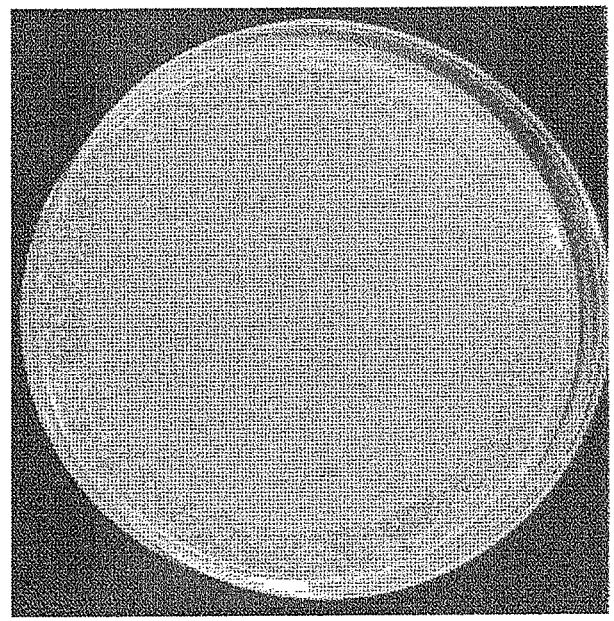
FIGS. 14A-14B are photographs taken to illustrate an effect of a filter module of a refrigerator according to an embodiment.
Figure 14:
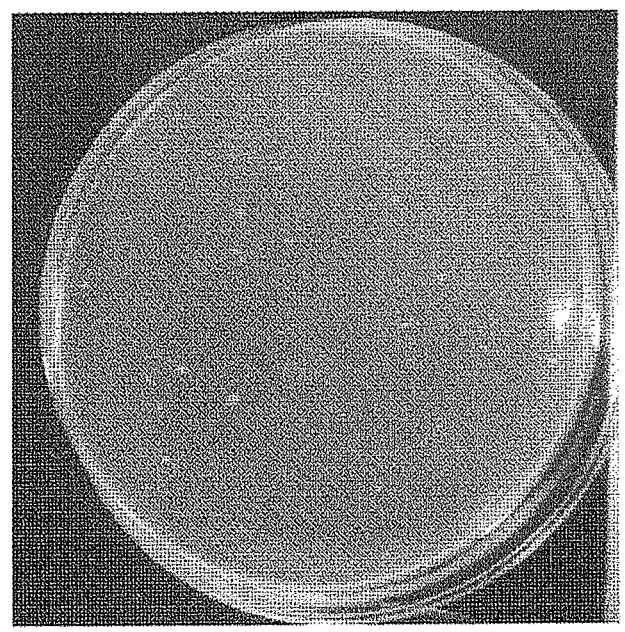
Figure 15:
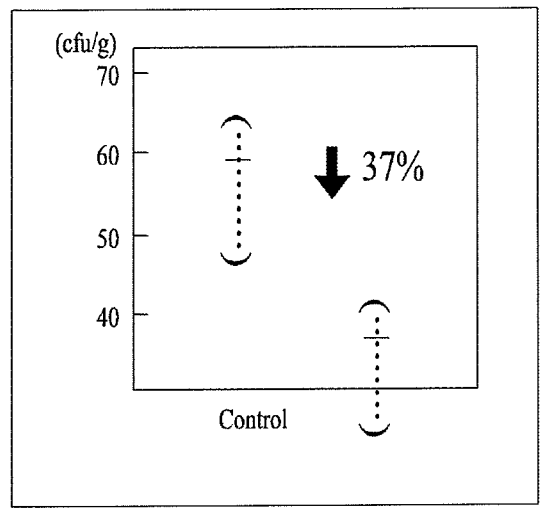
FIGS. 15A-15B are graphs illustrating an effect of a filter module of a refrigerator according to an embodiment.
Figure 15:
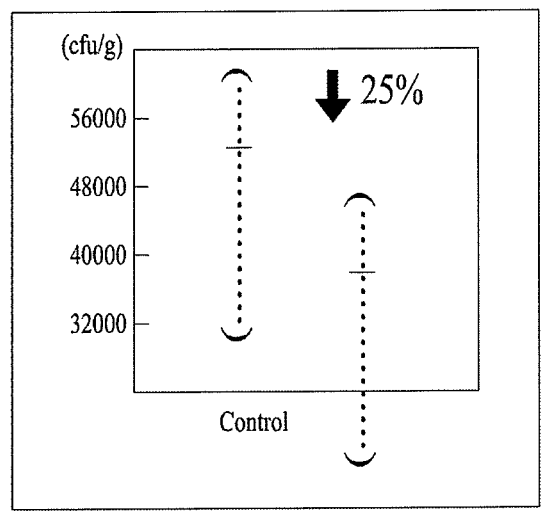

FIG. 10 is a block view of a refrigerator according to an embodiment. FIG. 11 is a diagram illustrating a control method of a refrigerator according to an embodiment. FIGS. 12A-12B and 13A-13B are graphs illustrating an effect of a filter module of a refrigerator according to an embodiment. FIGS. 14A-14B are photographs taken to illustrate an effect of the filter module of the refrigerator according to an embodiment. FIGS. 15A-15B are graphs illustrating an effect of the filter module of the refrigerator according to an embodiment.

FIG. 11 is a block view illustrating key parts of a control unit of a refrigerator relating to an embodiment.

The refrigerator 1 relating to this embodiment may include a control unit 80 configured to control operation of the filter module 100. The control unit 80 may be a central control unit to control an overall operation of the refrigerator or a local control unit to control only the operation of the filter module 100.

The control unit 80 may include an input part 81 to input a control command, such as on/off, and an operational mode of the filter module 100, and a display part 82 to display to the user a status of the storage room, an operational status of the filter module 100, or a replacement cycle of the filter module 100. In addition, the input part 81 may include a refrigerator compartment temperature adjusting part, a freezer compartment temperature adjusting part, and a special storage room temperature adjusting part. Also, the input part 81 may include an operational mode selecting part and a lock setting/unlock inputting part for each storage room.

The refrigerator 1 may include various sensors to acquire information on a status of the storage room 40. For example, it may include a temperature sensor 83 to measure a temperature of either of the storage rooms 40 and 50 and a door sensor 84 to determine whether to open the doors 20 and 30.

The status information of the storage room 40 may include at least one of operation mode information, operation temperature information, door opening information, lock-setting information, and abnormal status information. More specifically, the display part 82 may display an operation temperature for a specific storage section requiring special treatment (for example, a drawer and a storage box), together with an operation temperature for each of the refrigerator and freezer compartments.

The operation mode of the filter module 100 may include a manual mode in which the user inputs on/off selectively, if necessary, and an auto-mode, in which on/off is automatically implemented based on a preset operation condition.

Operation conditions of the auto-mode may be preset based on an integrated time of the compressor, a frequency, and/or a time of door opening.

According to one example, the control unit 80 may operate the filter module 100 for a predetermined time period, once a preset integrated time of the compressor has passed.

The control unit 80 may control the filter module to be on for a first time period and to be off for a second time period. The control unit 80 may repeat the on and off of the filter module multiple times. For example, the integrated time of the compressor may be approximately 5 hours. The first time period may be approximately 10 minutes and the second time period may be approximately 5 minutes.

Alternatively, the control unit 80 may control the filter module 100 to be driven for a preset time period based on opening and closing of the door 20, in other words, when the door 20 is opened and closed. The control unit 80 may control the filter module 100 to be driven for the preset time period when the door is closed, based on at least one of the opening/closing frequency of the door and the opening time of the door.

In other words, when the door is closed after being opened, it may be likely that food storage is performed and external air may be drawn into the storage room. Because of this, sterilization may be performed using the filter module 100.

With reference to FIG. 11, an example will be described in detail in which the filter module 100 is driven by the control unit 80 in an auto-mode according to an example.

First, considering the user's use status, the frequency and time of the door opening may increase in breakfast/lunch/dinner hours and operation conditions of the filter module 100 may be determined based on such actual use cycle. Also, an operation period of the compressor may be determined based on the actual use cycle mentioned above. The compressor may be driven for an approximately 8 hour period three times a day. The compressor may be stopped to operate for 3 hours after being driven for an integrated (accumulative) 5 hours.

The filter module 100 may be driven three times at intervals of approximately 8 hours according to the operation period of the compressor. In other words, when the filter module 100 may be automatically driven for approximately 2 (integrated) hours by the control unit 80, when the integrated time of the compressor is 5 hours. At this time, the filter module 100 may be operated for approximately 2 hours (8 times), repeating the driving for 10 minutes before stopping for 5 minutes.

Alternatively, the filter module 100 may be operated in a power mode when a large amount of food is stored in the storage room or strong sterilization is required. According to one example, the filter module may be operated for about 4 hours (16 times), repeating the driving for 10 minutes and stopping for 5 minutes (one time). In the meanwhile, the control unit 80 may stop the driving of the filter module, when the door is opened during the driving of the filter module 100, and it may drive the filter module 100 for the remaining time with the remaining frequency after the door is closed.

When a defrost operation starts during the driving of the filter module 100, the control unit 80 may stop the driving of the filter module. The control unit 80 may drive the filter module 100 for the remaining time with the remaining frequency after the defrost operation has finished.

Figure 12:
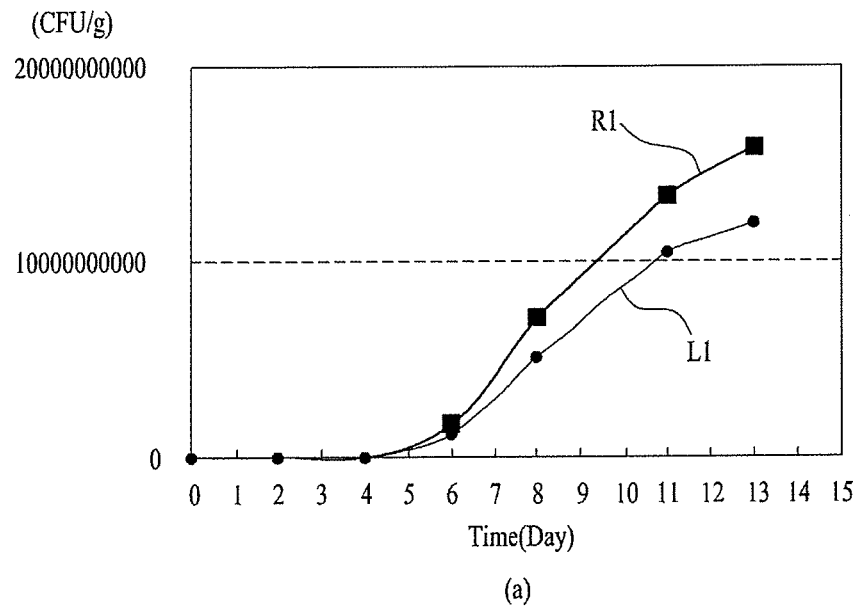
FIGS. 12A-12B and 13A-13B are graphs illustrating an effect of the filter module of a refrigerator according to an embodiment.
Figure 12:
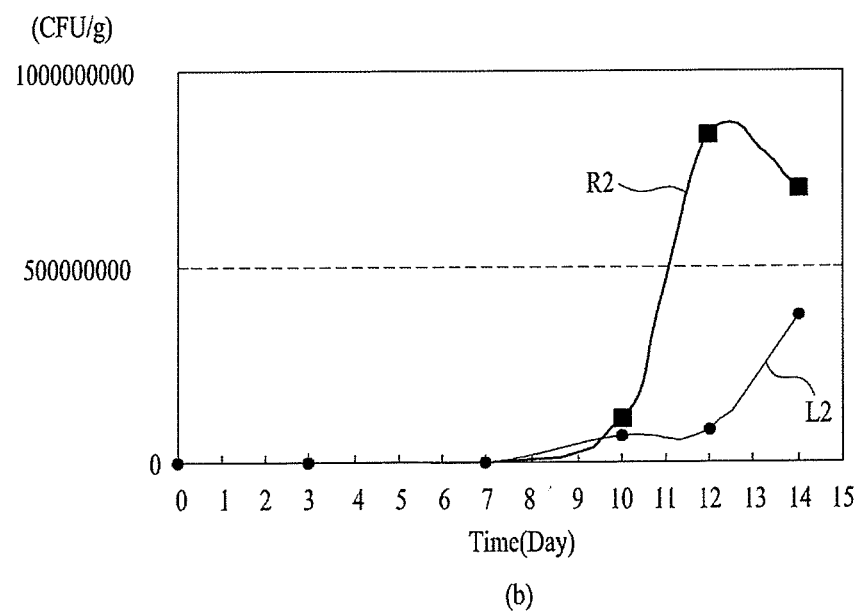
Figure 13:
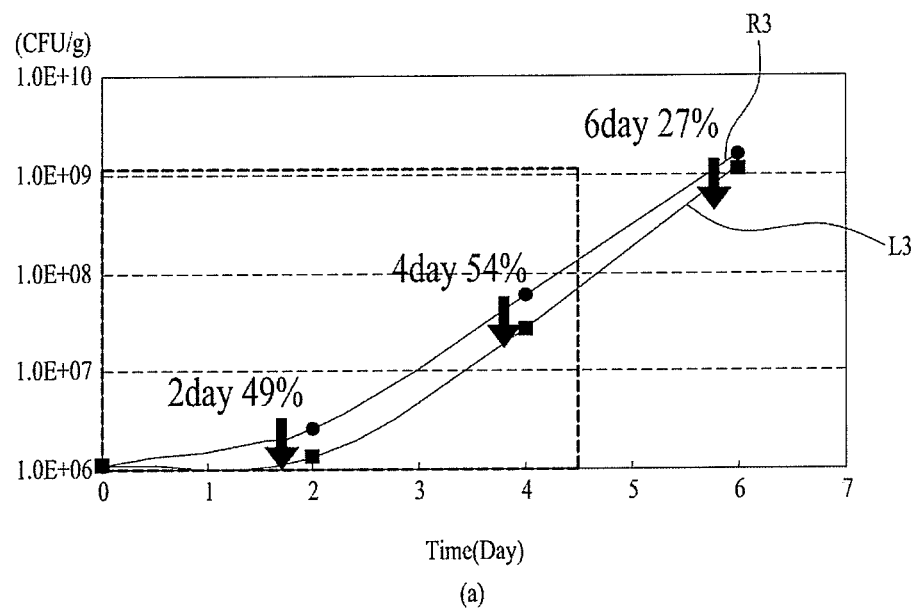
Figure 13:
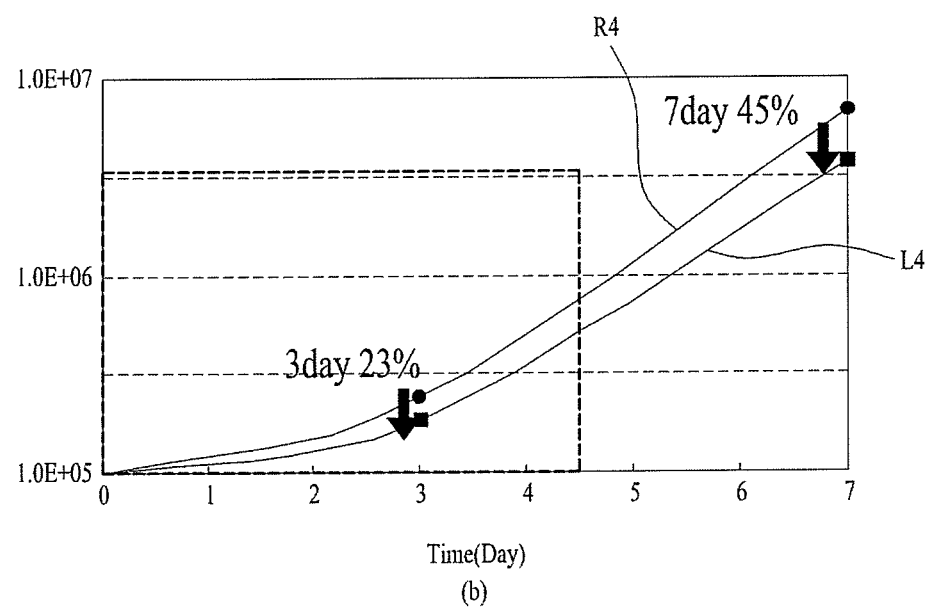

FIGS. 12A-12B and 13A-13B are graphs to describe a sterilization effect of the refrigerator 1 relating to an embodiment. FIGS. 12A and 13A illustrate experimental data, targeted at chicken and FIGS. 12B and 13B illustrate experimental data, targeted at beef.

With reference to FIGS. 12A-12B, "R1" and "R2" refer to the viable microbe cell number according to passage of days when the filter module 200 is not applied. "L1" and "L2" refer to the viable microbe cell number according to passage of days when the filter module 100 is applied. With reference to FIG. 12A, approximately 32% of the viable microbe cell number may be decreased after 14 days when the filter module 100 is applied. With reference to FIG. 12B, approximately 91% of the viable microbe cell number may be decreased after 14 days when the filter module 100 is applied.

With reference to FIGS. 13A-13B, "R3" and "R4" refer to the viable microbe cell number according to passage of days when the compound of kimchi lactobacillus extract and protein activity inhibitor is not coated on the filter module 100. "L3" and "L4" refer to the viable microbe cell number according to passage of days when the compound of kimchi lactobacillus extract and protein activity inhibitor is coated on the filter module 100. With reference to FIG. 13A, it is shown that approximately 49% of the viable microbe cell number is decreased after 2 days, when the compound of kimchi lactobacillus extract and protein activity inhibitor is coated on the filter module 100. In reference to FIG. 13B, it is shown that approximately 23% of the viable microbe cell number is decreased after 3 days, when the compound of kimchi lactobacillus extract and protein activity inhibitor is coated on the filter module 100.

With reference to FIGS. 14A-14B, FIG. 14A is a photograph of an air sample collected after being forcibly circulated by the fan, with spraying bacteria, when the filter module 100 is not applied to a preset experiment chamber, and FIG. 14B is a photograph of an air sample collected after forcibly circulated to pass the filter module 100 by the fan, with spraying bacteria, when the filter module 100 is applied to a preset experiment chamber. According to the photographs, it is shown that approximately 99.8% of the bacteria are reduced when the filter module 100 is applied.

FIGS. 15A-15B is graphs illustrating decrease of contaminants when the filter module 100 is operated after arranged in a storage room of a refrigerator. FIG. 15A illustrates an effect in case of performing an experiment that uses microbial medium, and it is shown that approximately 37% of microbes are decreased. FIG. 15B illustrates an effect in case of performing an experiment that uses chopped chicken, and it is shown that approximately 25% of microbes are decreased.

Also, experimental data for a decreasing rate of various microbes in case of using the filter module 100 is as follows:

TABLE 1

| Experiment Method | Experiment Protocol | Experiment Environment | Microbe | Decreasing Rate | | | |
|---|---|---|---|---|---|---|---|
| | | | | 0 min. | 15 min. | 30 min. | 60 min. |
| Shaking flask | ASTM E2149-01 | 35% | E. coli ATCC 11229 | 65.57% | 99.98% | >99.98% | >99.99% |
| | | | S. aureus ATCC 6538 | 25% | 91.25% | 99.42% | >99.99% |
| | | | S. enteria ATCC 13311 | >99.95% | >99.99% | >99.99% | >99.99% |
| | | | L. monocytogenes ATCC 19114 | 63.13% | 60.71% | >99.99% | >99.99% |
| Shaking Flask | ASTM E2149-01 | 3% | E. coli ATCC 11229 | 21.43% | 7.41% | 71.07% | 92.86% |
| | | | S. aureus ATCC 6538 | | >99.99% | 37.04% | 69.26% |
| | | | S. enteria ATCC 13311 | 99.79% | 21.05% | >99.99% | >99.99% |
| | | | L. monocytogenes ATCC 19114 | 10.53% | 21.05% | 26.32% | 76.84% |

TABLE 2

| Experiment Method | Protocol | Experiment Environment | Microbe | Decreasing Rate (After 24 hours) |
|---|---|---|---|---|
| Shaking flask | FITI FC-TM-19 | 35% | E. coli ATCC 11229 | >99.99% |
| | | | S. aureus ATCC 6538 | >99.99% |
| | | | S. enteria ATCC 13311 | >99.99% |
| | | | L. monocytogenes ATCC 19114 | >99.99% |
| | | | Feline calicivirus | >99.99% |

TABLE 3

| Experiment Method | Protocol | Experiment Environment | Microbe | Decreasing Rate (After 24 hours) |
|---|---|---|---|---|
| Shaking flask | FITI FC-TM-19 | 4% | E. coli ATCC 11229 | >99.99% |
| | | | S. aureus ATCC 6538 | 88.70% |
| | | | L. monocytogenes ATCC 19114 | 94.20% |

As mentioned above, according to the refrigerator relating to at least one embodiment, food stored in the storage room and air inside the storage room may be sterilized effectively, to keep the storage room clean.

Figure 16:
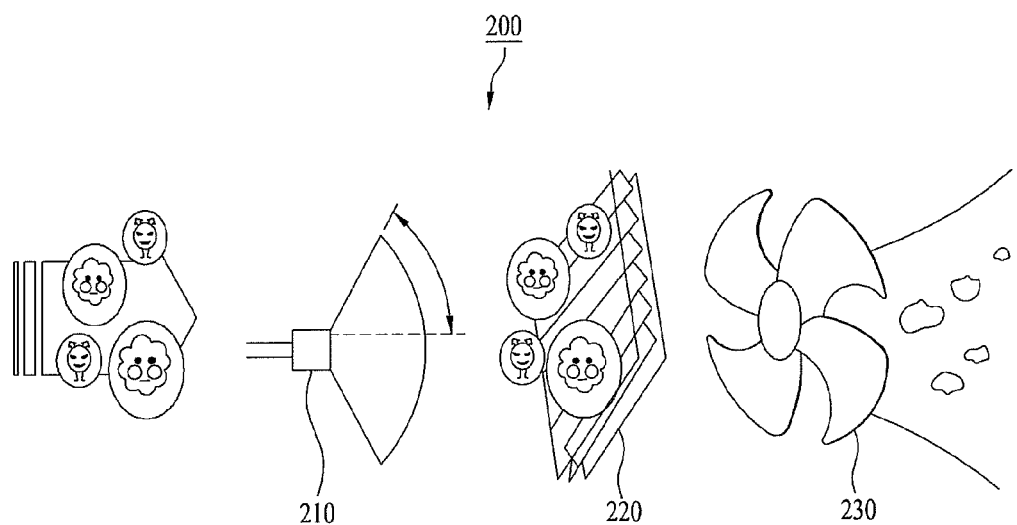
FIG. 16 is a conceptual diagram illustrating a filter module of a refrigerator according to an embodiment.
Figure 17:
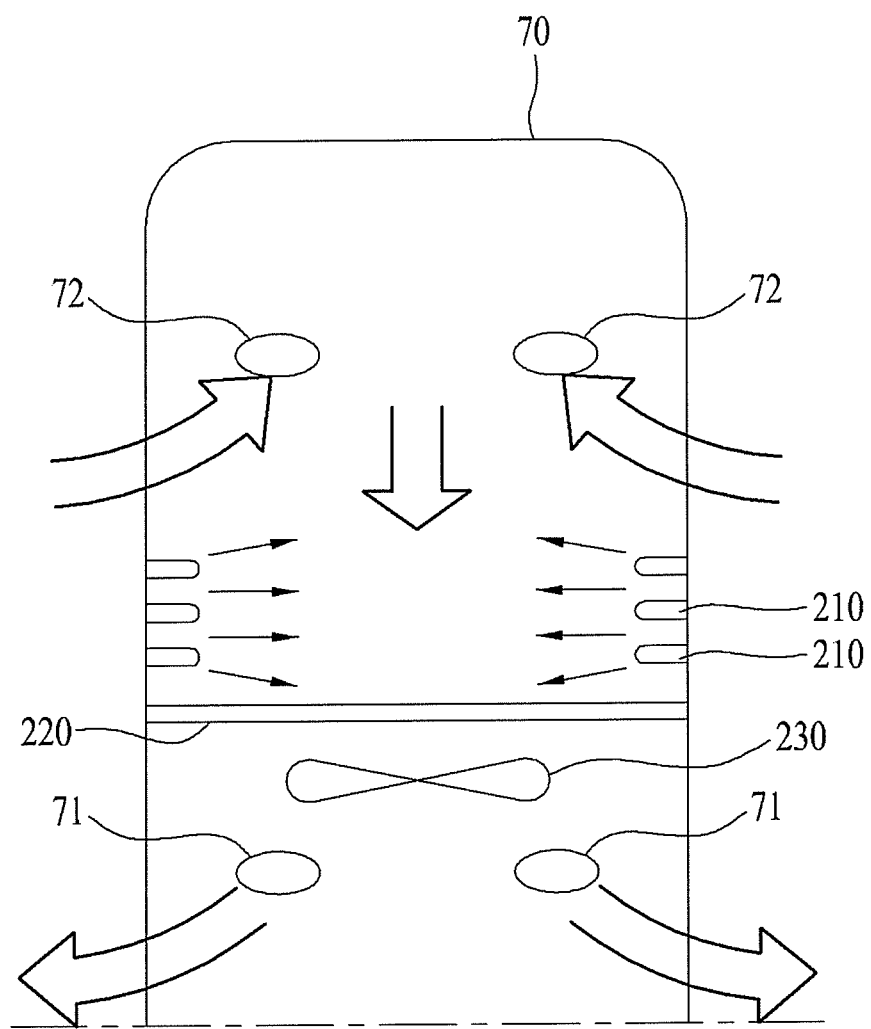
FIG. 17 is a plane view illustrating the filter module and the multi duct of FIG. 16.

FIG. 16 is a conceptual diagram illustrating a filter module of a refrigerator according to an embodiment. FIG. 17 is a plane view illustrating the filter module and the multi duct shown in FIG. 16. The refrigerator according to this embodiment may include a case having at least one storage room for low temperature storage, a compressor provided in the case to compress refrigerant, at least one door to open and close the storage room, a filter module 200 having at least one UV lighting source 21 to irradiate UV light toward the storage room and a photocatalyst filter 220 to filter the air having the UV irradiated thereto, and a control unit to control operation of the filter module 200.

The refrigerator according to this embodiment is the same as the refrigerator according to the embodiment mentioned above, except for the filter module. As follows, the only difference will be described in detail and description of the other repeated components will be omitted accordingly.

Titanium may be coated on the photocatalyst filter 220. With reference to FIG. 16, the UV lighting source 210 may irradiate UV light toward the air inside the storage room. Once bacteria contained in the air is dead because of the UV light, remnants of the dead bacteria may decompose because of the titanium-coated photocatalyst filter 220. As a result, the filter module 200 may have a remnants-removing effect, as well as a sterilization effect.

Also, the filter module 200 may further include an anti-allergen filter. The anti-allergen filter is the same as described above.

In the meanwhile, the filter module 200 may have various structures. According to one example of the structure, the filter module 200 may include a housing (not shown) having an air inlet and an air outlet formed therein, and a fan 230 arranged adjacent to the air outlet of the housing. The UV lighting source 210 may be arranged adjacent to the air inlet inside the housing, and the photocatalyst filter 220 may be arranged adjacent to the air outlet inside the housing.

As it is the same as the refrigerator mentioned above with reference to FIGS. 2 to 6, the case of the refrigerator may include an inner case that defines the storage room and an outer case that defines an exterior appearance of the refrigerator. A cold air duct 60 and a filter duct 70 (second duct) may be provided in a predetermined space formed between the inner case and the outer case to provide cold air to the storage room and to provide a passage for sterilization, respectively.

With reference to FIG. 17, the filter module 200 may be arranged in the filter duct 70 (second duct). In this case, an inlet 72 to draw air inside the storage room and an outlet 71 to exhaust the sterilized air to the storage room may be provided in the filter duct 70 (second duct).

According to one example, a plurality of the UV lighting source 210 may be arranged in an inner circumferential surface of the filter duct 70 (second duct), spaced apart a proper distance from each other, to irradiate UV light toward the air. A fan 230 may be arranged in the filter duct 70 (second duct).

Also, a passing hole may be provided in the inner case, corresponding to the outlet 71 of the filter duct 70 (second duct). The sterilized air may be drawn into the inner case via the passing hole.

As mentioned above, the inner case may be partitioned into a plurality of storage sections. At least one passing hole of the inner case may be provided for each of the storage sections. In other words, the sterilized air may be supplied to each of the storage sections via the filter duct 70 (second duct) as mentioned above.

The UV lighting source 210 may be operated based on at least one of a light emitting time, a light emission intensity, and a light emission period that are stored in the control unit. The UV lighting source 210 may be operated based on at least one of an opening status of the door, and a change in temperature inside the storage room.

Also, the control unit may include an input part to input control commands, such as on and off, of the UV lighting source, a light emission duration time, a light emission intensity (for example, strong, middle and weak), and a light emission period, and a display part to display a status of the storage room. In addition, the input part may include a refrigerator compartment temperature adjusting part, a freezer compartment temperature adjusting part, and a special storage room temperature adjusting part. Also, the input part may include an operational mode selecting part and a lock setting/unlock inputting part for each storage room.

The status information of the storage room may include at least one of operation mode information, operation temperature information, door opening information, lock-setting information, and abnormal status information. More specifically, the display part may display an operation temperature for a specific storage section requiring special treatment (for example, a drawer and a storage box), together with an operation temperature for each of the refrigerator and freezer compartments.

Also, the display part may be a liquid crystal display, and it may be configured of a plurality of light emitting diodes (LED) capable of displaying numbers, characters, and various symbols.

The UV lighting source 210 may be operated based on at least one of the light emission duration time, the light emission intensity (for example, strong, middle and weak), and the light emission period stored in the control unit. The light emission duration time, the light emission intensity, and the light emission period may be preset by the user, such that the UV lighting source 210 may be controlled by the control unit constantly (auto-mode). Alternatively, they are input by the user at the time when he or she desires to drive the UV lighting source 210, such that the UV lighting source 210 may be controlled intermittently (manual-mode).

The control unit may control operation of the UV lighting source 210 based on a temperature change inside the storage room. According to one example, when the temperature of the storage room is a predetermined reference value or more, the control unit may operate the UV lighting source 210 for a preset time period.

The reference value may be determined based on a result of experiments, for example, 2 to 6, and it may be approximately 3. When the temperature change inside the storage room is the reference value or more, the control unit may expect that the food stored in the storage room could be contaminated, and it may then operate the UV lighting source 210.

The control unit may control the operation of the UV lighting source based on an opening status of the door, an opening frequency of the door, or an opening time of the door. For example, the control unit may operate the UV lighting source 210 for a preset time period after the door is opened and closed, and it may not operate the UV lighting source 21 until the door is open and closed the next time.

In other words, there might be concern of contamination that can occur to food contained in the storage room when new food is accommodated in the storage room. Because of this, the control unit may control the operation of the UV lighting source 210 based on the status of the door opening, the frequency of the door opening or the duration time of the door opening.

In the meanwhile, so far, the embodiment that the operation of the UV lighting source 210 is controlled based on the status of the door opening or temperature change inside the storage room is described, but the present invention is not limited thereby. The operation of the UV lighting source 210 may be controlled based on both of the door opening status and the storage room temperature change.

For example, when the temperature inside the storage room is increased up to a reference value or more after the door is open and closed, the control unit may operate the UV lighting source 210 for a preset time period. Until the temperature inside the storage room is increased up to the reference value or more after the door is open and closed next time, the control unit may not operate the UV lighting source 210.

When the UV lighting source 210 is operated in the refrigerator constantly, plastic material inside the refrigerator (an inner circumferential surface of the storage room and a food container) might be discolored even after the sterilization. Because of this, a replacing interval of the plastic material happens fast.

As a result, according to the refrigerator 1 according to the first embodiment described above, the filter module 200 may be arranged in the filter duct 70 (second duct). Because of this, discoloration generated in the inner circumferential surface of the storage room and the food container may be prevented and usage of the UV lighting source 210 may be lengthened.

Also, in a case of concern over contamination of food, sterilization may be selectively performed based on the introduction of food or internal temperature change. Because of this, power consumption may be reduced.

Figure 18:
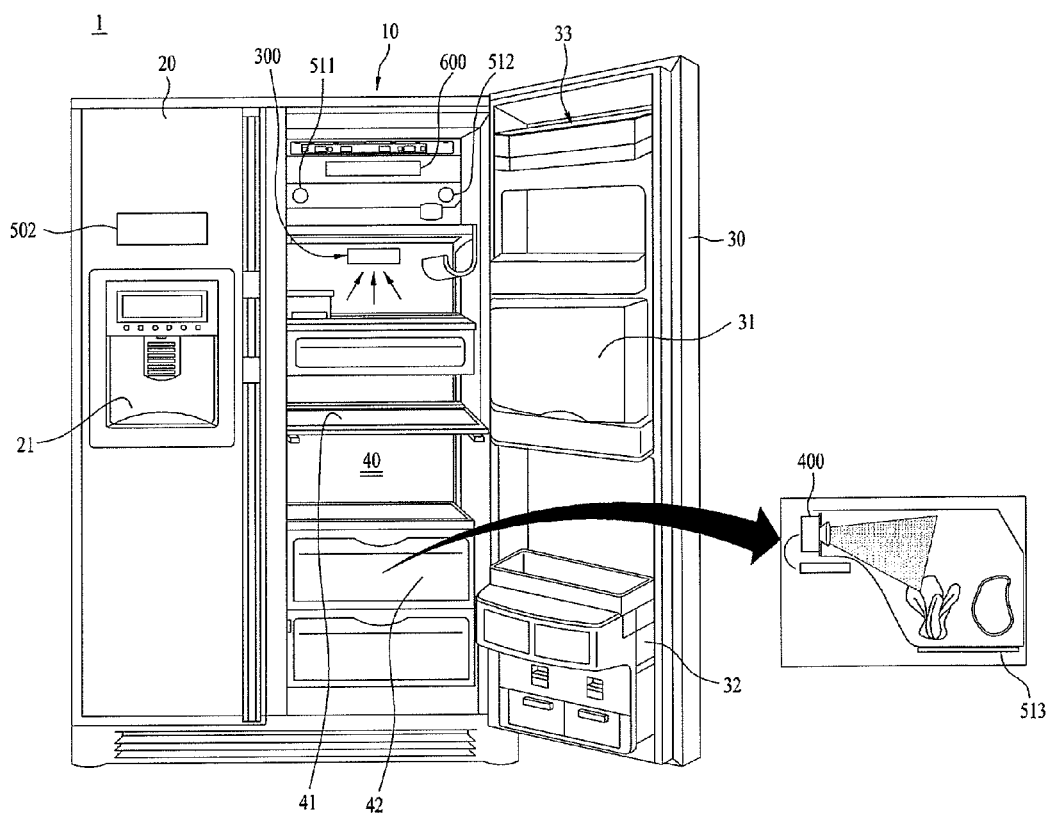
FIG. 18 is a perspective view illustrating a door of a refrigerator according to a further embodiment, which is partially open.
Figure 19:
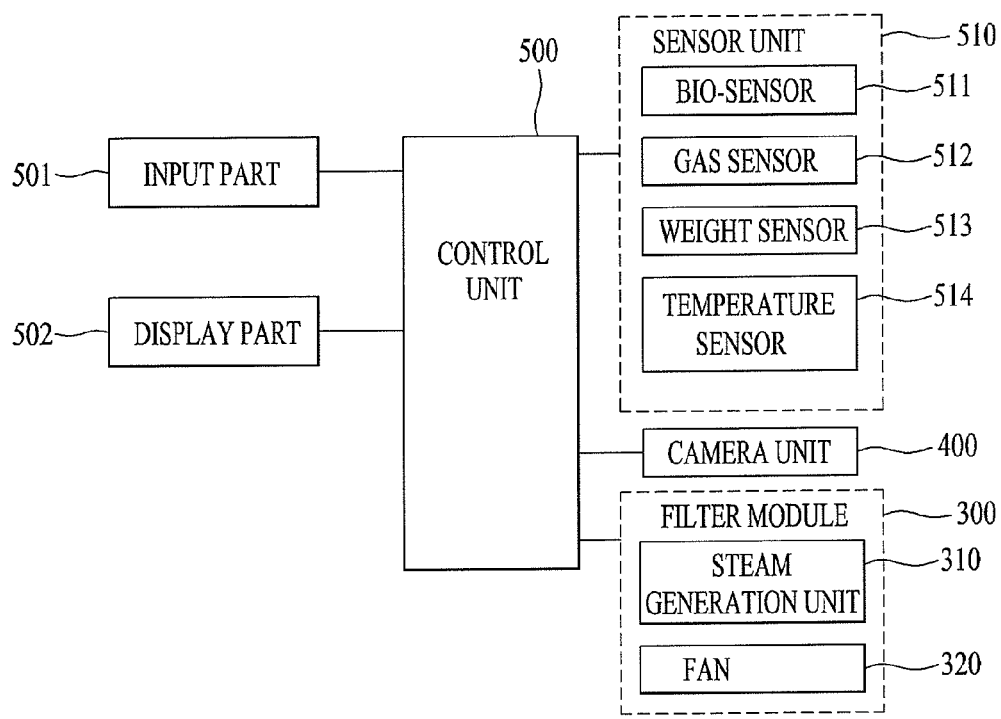
FIG. 19 is a block view illustrating the refrigerator of FIG. 18.
Figure 20:
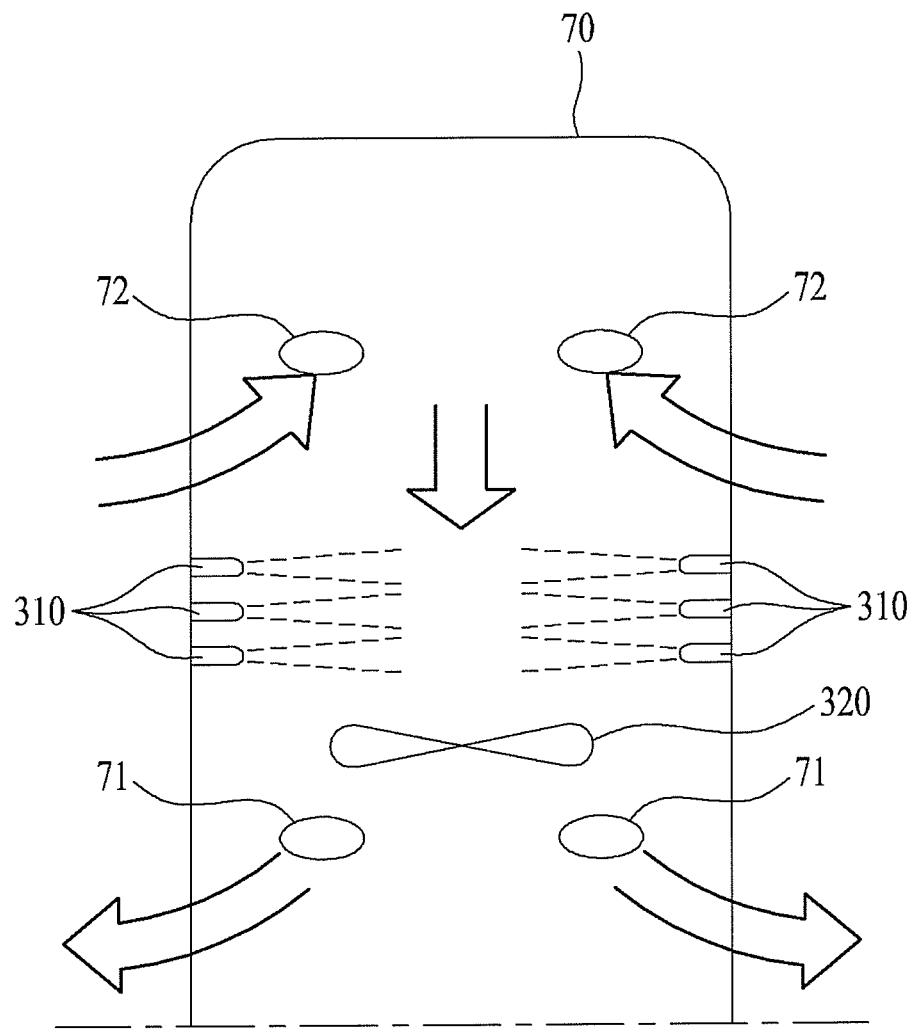
FIG. 20 is a plane view illustrating a filter module and a multi duct of the refrigerator of FIG. 18.
Figure 21:
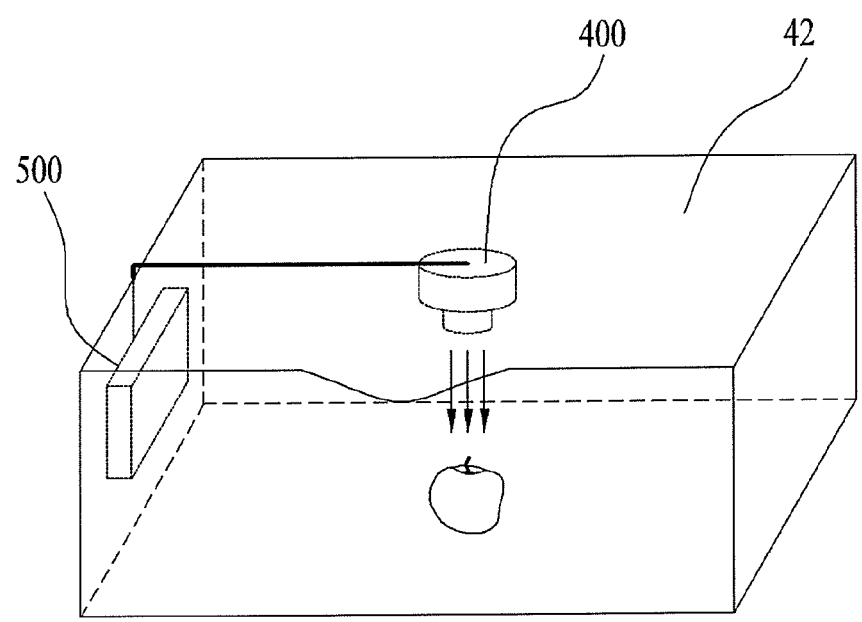
FIG. 21 is a perspective view illustrating key parts of a camera unit of the refrigerator of FIG. 18.

FIG. 18 is a perspective view illustrating a door of a refrigerator according to a further embodiment, which is partially open. FIG. 19 is a block view illustrating a refrigerator according to the embodiment of FIG. 18. FIG. 20 is a plane view illustrating a filter module and a multi duct of the refrigerator of FIG. 18. FIG. 21 is a perspective view illustrating key parts of a camera unit of the refrigerator of FIG. 18.

A refrigerator 1 according to this embodiment may include a cabinet 10 having an inner case defining at least one storage room formed therein for low temperature storage of food and an outer case defining an exterior appearance thereof, a sensor unit 510 detecting a source of contamination inside the storage room, and at least one door 20 and 30 selectively opening and closing the storage room.

Also, the refrigerator may include a filter duct 70 (second duct) arranged between the inner case and the outer case to flow air inside the inner case therein, a filter module 300 having a steam generation unit 310 provided in the filter duct 70 (second duct) to spray high temperature gas toward the air drawn into the filter duct 70 (second duct) and a fan 320 to adjust air flow inside the filter duct 70 (second duct), and a control unit 500 to control operation of the filter module 300 based on the result of the detection performed by the sensor unit 510.

The refrigerator 1 of this embodiment is the same as the refrigerator according to the embodiment described with reference to FIG. 1, except for the sensor unit 510 and the filter module 300. As follows, the difference will be described in detail and the other repeated description of the same components will be omitted accordingly.

The sensor unit 510 may include at least one of a bio-sensor 511 to detect a specific bacteria contaminant and a gas sensor 512 to detect an offensive smell factor. As mentioned above, the sensor unit 510 may include a weight sensor 513 to measure the weight of the stored goods (for example, food) seated in the storage room and a temperature sensor 514 to identify information on a status inside the storage room 40.

In addition, the refrigerator 1 may further include a microbial response viewer (MRV) system 600 that is a simulation program configured to manage microbes for each kind of food based on temperature, pH, humidity, Aw, and the surrounding environments. The MRV system 600 may perform a function of analyzing the kind and amount of the bacteria detected by the bio-sensor 511.

The control unit 500 may include an input part 501 to input control commands relating to the operation of the filter module, such as on and off, of the steam generation unit and the fan, a steam spray time, a steam intensity (for example, strong, middle and weak), and a steam spray period, and a display part 502 to display a status of the storage room.

The input part 501 may include a refrigerator compartment temperature adjusting part, a freezer compartment temperature adjusting part, and a special storage room temperature adjusting part. Also, the input part may include an operational mode selecting part and a lock setting/unlock inputting part for each storage room.

The display part 502 may display an operation temperature for a specific storage section requiring special treatment (for example, a drawer and a storage box), together with an operation temperature for each of the refrigerator and freezer compartments. One of the doors (for example, the door 20) may have the display part 502 arranged in an outer circumferential surface thereof.

The bio-sensor 511 may be an optical type bio-sensor and it may be able to detect food-poisoning bacteria located in the refrigerator. The gas sensor 512 may detect an offensive smell factor generated in the storage room 40. When the detected smell factor is a preset concentration or more, the control unit 500 may drive the filter module 300.

Also, the control unit 500 may determine a spraying time and steam temperature of the filter module based on the kind and amount of the bacteria detected by the bio-sensor 511 and the MRV system 600. The control unit 500 may control the display part 502 to display a contamination status inside the storage room that is detected by the sensor unit 510 to the user.

With reference to FIG. 20, the filter module 300 may be arranged in the filter duct 70 (second duct). In this case, an inlet 72 to draw air inside the storage room and an outlet 71 to exhaust the sterilized air to the storage room may be provided in the filter duct 70 (second duct).

According to one example, a plurality of the steam generating units 310 may be arranged in an inner circumferential surface of the filter duct 70 (second duct), spaced apart a proper distance from each other, to spray high-temperature steam toward the air. A fan 320 may be arranged in the filter duct 70 (second duct).

Also, a passing hole may be provided in the inner case, corresponding to the outlet 71 of the filter duct 70 (second duct). The sterilized air may be drawn into the inner case via the passing hole.

As mentioned above, the inner case may be partitioned into a plurality of storage sections. At least one passing hole of the inner case may be provided for each of the storage sections. In other words, the sterilized air may be supplied to each of the storage sections via the filter duct 70 (second duct) as mentioned above.

Once the steam spraying is complete, the control unit 500 may increase a cooling load of the storage room for a preset time period. In other words, when the high-temperature steam is sprayed to the cold air inside the storage room to perform the sterilization, the temperature inside the storage room may be increased, and there might be concern about food spoiling, which has to be prevented in advance.

With reference to FIG. 21, the sensor unit 510 may include a camera unit 400 arranged in a storage room 42 to detect an image of the stored food to visualize the stored food. The control unit 500 may determine spoiling of the stored food based on a difference between an image of the stored food memorized in advance and the image of the stored food detected by the camera unit 400. The camera unit 400 may detect at least one of temperature, color, and shape of the stored food.

Also, the display part 502 may image surface temperature distribution of the visualized stored food to display the imaged surface temperature distribution to the user. Also, the display part 502 may display the result of determination on the spoiling of the stored food performed by the control unit 500 to the user.

The camera unit 400 may detect and visualize images of fruit or vegetables stored in the storage room (for example, the drawer 42). In other words, the refrigerator 1 relating to this embodiment may analyze freshness and spoiling of stored food nondestructively using image processing technology. The control unit 500 may process the acquired image information and display the processed information to the user via the display part 502.

With reference to FIG. 21, according to one example, the control unit 500 may determine whether a stored apple is spoiled based on a difference among distributed surface temperatures of the apple visualized by the camera unit 400. In other words, a surface temperature of a plant may be determined by an environmental factor and transpiration (evaporative water via stomata of a plant emits extra heat). If a plant tissue damages because of various stresses, the plant closes the stomata and the closed stomata fails to perform the transpiration. The damaged tissue that fails to generate the transpiration may fail to emit the heat. Because of this, a surface temperature of the plant may increase.

Figure 22:
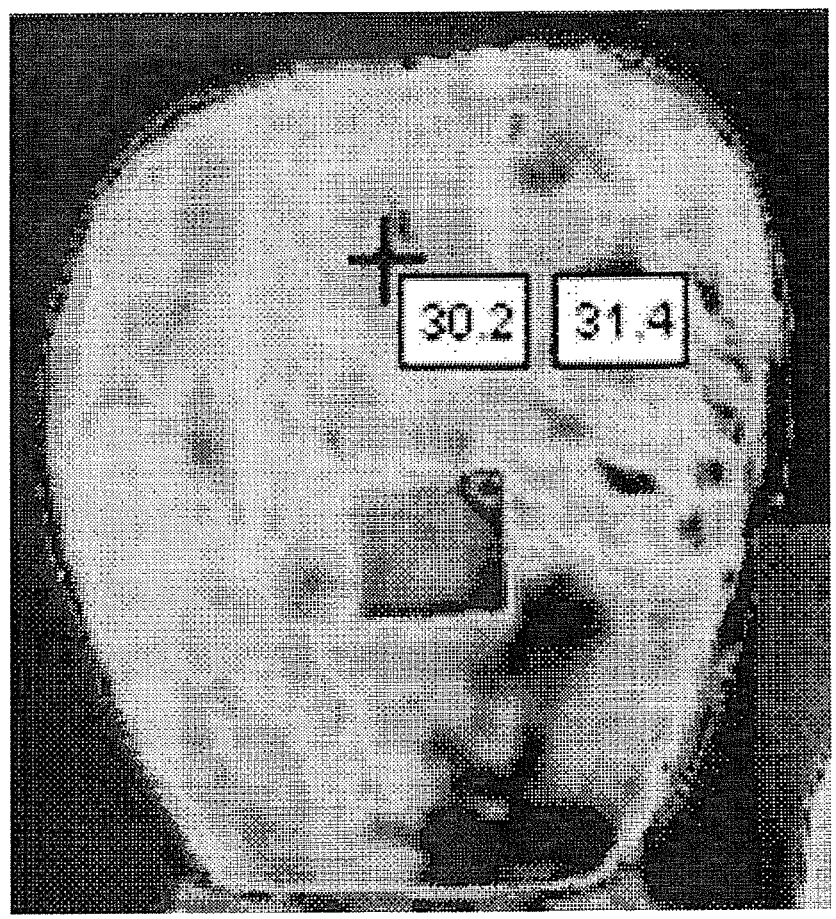
FIGS. 22 to 25 are photographs taken to illustrate an example of an operation status of the camera unit shown in FIG. 21.
Figure 23:
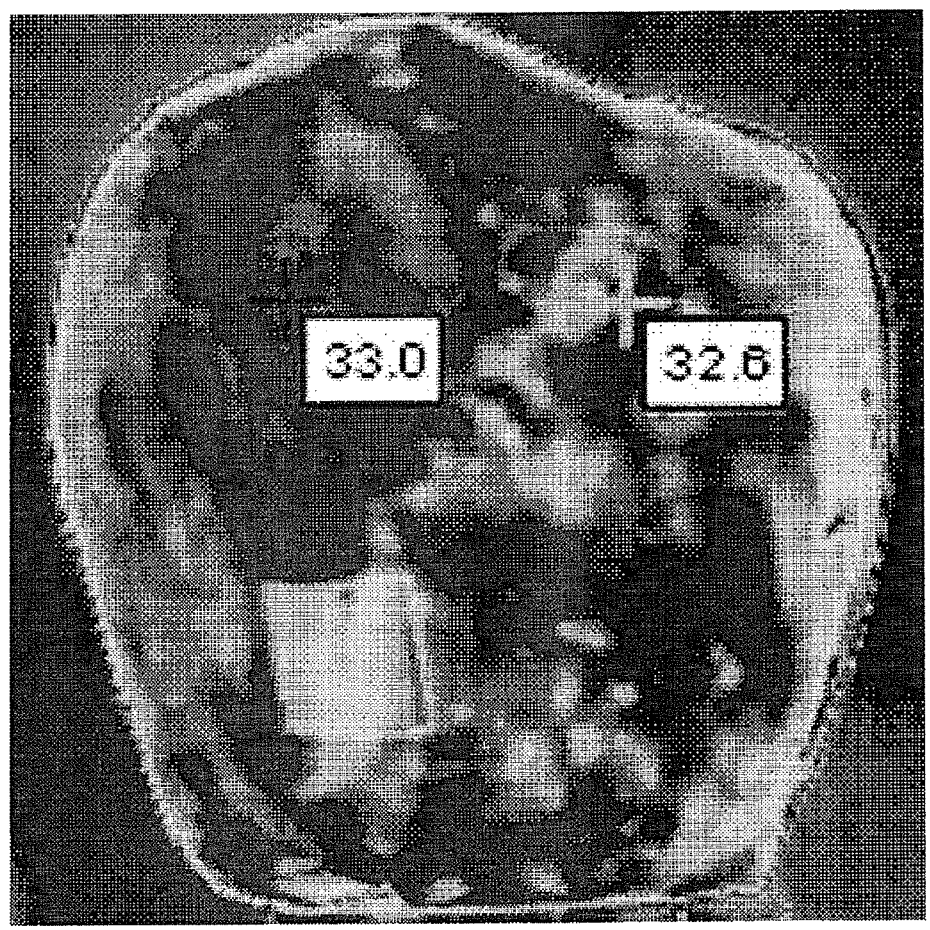

FIGS. 22 to 25 are photographs taken to illustrate an example of an operation status of the camera unit of FIG. 21. With reference to FIGS. 22 and 23, the control unit 500 may control the camera unit 400 to visualize surface temperature distribution of fruit and vegetables stored in the storage room 42 every preset time. The control unit 500 may compare the surface temperatures of the fruit and vegetables with each other. When the difference among the surface temperatures is out of a preset temperature range, the control unit 500 may determine that the fruit and vegetables are spoiled.

The camera unit 400 may detect an infrared light radiated from the fruit and vegetable according to active thermography and passive thermography. That is, according to the active thermograph, a heat source is supplied to an object and an infrared light radiated from the object is detected. According to the passive thermograph, an infrared light self-radiated from the object is detected.

As a result, when the surface temperature distribution of the fruit and vegetables is visualized according to the active thermograph, a heat source part (not shown) may be provided in the storage room 42 to supply heat to the, fruit and vegetables stored in the storage room 42. The camera unit 400 may detect an infrared light radiated from the vegetables and the fruits supplied the heat by the heat source part, to visualize the surface temperature distribution. When the surface temperature distribution of the fruit and vegetables is visualized according to the passive thermograph, the camera unit 400 may detect an infrared light self-radiated from the fruit and vegetables supplied the heat by the heat source part, to visualize the surface temperature distribution.

The display part 502 provided in an outer surface of the door 20 may image surface temperature distribution of the fruit and vegetables visualized by the camera unit 400, and it may display the imaged surface temperature distribution to the user at a predetermined interval. As a result, the user may recognize a quality status of the fruit and vegetables stored currently by looking at the surface temperature distribution of the fruit and vegetables stored in the storage room 42 via the display part 502.

The surface temperature distribution of the fruit and vegetables that is visualized by the camera unit 400 may be memorized in a memory part (not shown). The control unit 500 may determine the spoiling of the fruit and vegetables stored in the storage room 42 based on the difference among the distributed surface temperatures stored in the memory part. That is, when the surface temperature distribution of the fruit and vegetables measured at preset intervals is out of a preset temperature range, the control unit 500 may determine that tissues of the fruit and vegetables are damaged.

With reference to FIG. 22, fruit, such as an apple, may acquire a yellow color generally, to have a relatively low surface temperature distribution. However, as time passes, the tissue of the apple may be damaged and the stomata closed. Because of this, the transpiration fails to happen and the surface temperature of the apple increases.

With reference to FIG. 23, when the tissue of the fruit, such as an apple, is damaged as time passes, the fruit may acquire a red color around the damaged tissue to have a relatively high surface temperature distribution. In this case, the control unit 500 may compare the imaged surface temperature distribution of the apple before a preset time passes with the imaged surface temperature distribution after the preset time has passed. If the difference of the surface temperature distributions is out of a preset temperature range, the control unit may determine that the tissues of the fruit and vegetables are damaged.

When determining that the tissues of the fruit and vegetables are damaged, the control unit 500 may display the spoiling of the fruit and vegetables to the user via the display part 502, and it may also display a message of consuming or discarding the fruit and vegetables. As a result, the user can discard or consume right away when the tissues of the fruit and vegetables stored in the storage room 42 are damaged. In a case that the fruit and vegetables are spoiled, the spoiled fruit and vegetables may be removed from the refrigerator and generation of offensive smell may be prevented. Also, the possibility of the user's suffering from a disease caused by eating of the spoiled fruit and vegetables may be reduced.

Figure 24:
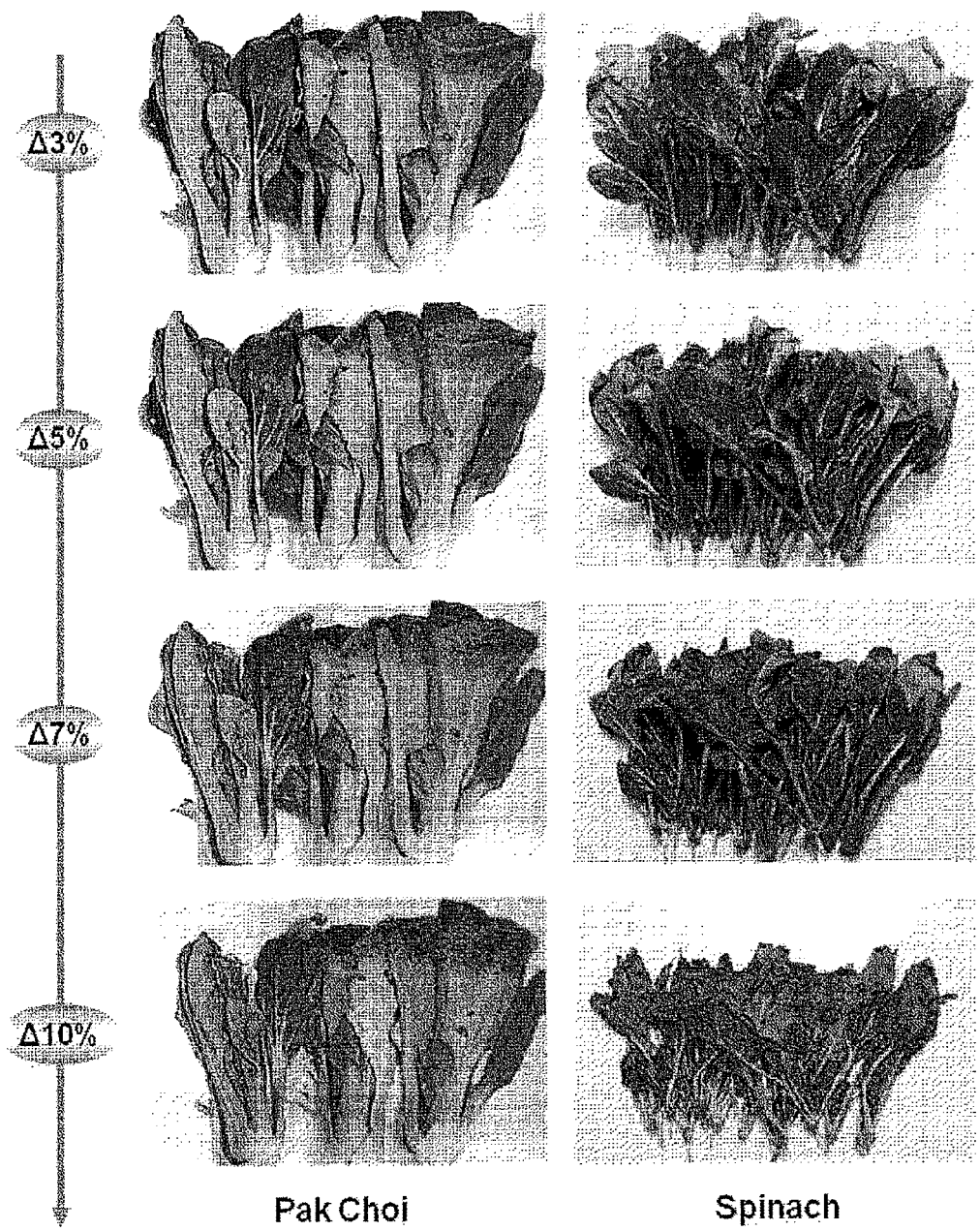

FIG. 24 includes photographs showing change in shape and color of food stored in the storage room 42 provided in the refrigerator according to this embodiment, for example, spinach and pac-choi. With reference to FIG. 24, vegetables, such as spinach and pac-choi, acquire a green color generally right after being stored in the storage room 42, which means that a fresh status is maintained.

However, as a preset time period passes, tissues of the spinach and the pac-choi are damaged, and the color of spinach and the pac-choi is changed because of oxidation. In other words, as shown in the lower photographs of FIG. 24, a yellow color may increase around the damaged tissues and an original color thereof may fade gradually, if the tissues of the spinach and the pac-choi are damaged.

In this case, the control unit 500 may compare an imaged surface color of the spinach and pac-choi before a preset time period has passed and an imaged surface color thereof after the preset time period has passed. When the difference between the surface colors is out of a preset color range, the control unit 500 may determine that the tissues of the fruit and vegetables are damaged.

Figure 25:
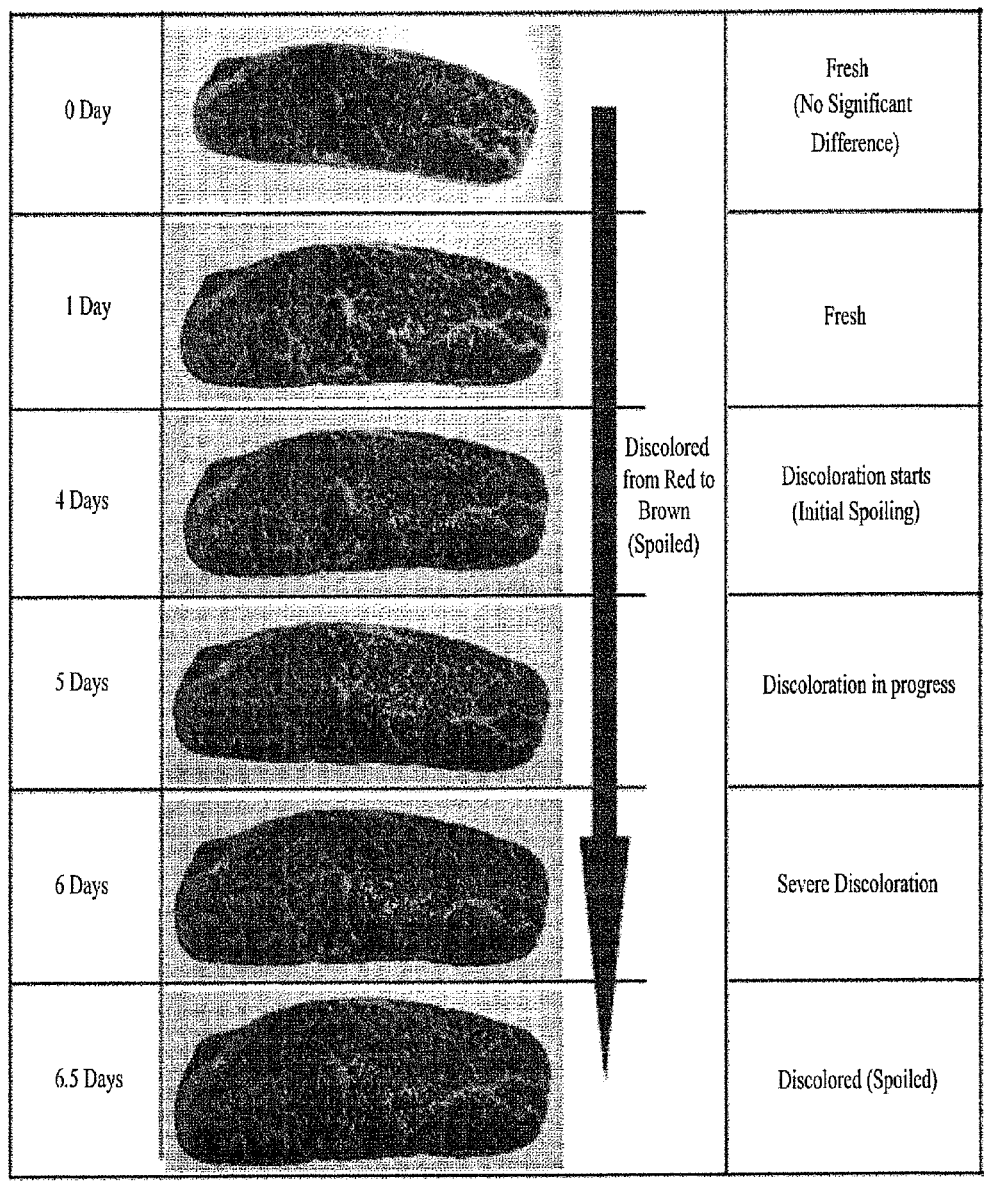

With reference to FIG. 25, according to another example, when meat, such as pork and beef, is stored in the storage room 42, an overall shape of the meat right after being stored in the storage room may be maintained almost the same as a shape of an outer surface of the meat.

However, as time passes, tissues of the meat may be damaged and juice may come out of the meat. Because of this, an overall outer shape of the meat may change at a surface at which the juice collects.

In this case, the control unit 500 may compare imaged shapes of the meat before and after a preset time has passed with each other. When a difference between the shapes is out of a preset shape range, the control unit 500 may determine that the tissues of the meat are damaged.

A user may change the preset shape range to a desired range by using the button part 220.

When determining that the tissues of the meat and the tissues of the fruit and vegetables are damaged, the control unit 500 may display to the user that juice is coming out of the meat, and that the color of the fruit and vegetables has changed via the display part 502. At the same time, the control unit 500 may display a message of consuming or discarding the meat and the fruit and vegetables.

As a result, when the tissues of the meat and the fruit and vegetables stored in the storage room 42 are damaged, the user may consume or discard them immediately. Because of this, the spoiled food may be removed from the refrigerator quickly if the food is spoiled, and offensive smells may be prevented.

Also, the possibility of the user's suffering from a disease caused by eating spoiled meat, fruit, and vegetables may be reduced.

As described above, according to the refrigerator relating to at least one embodiment, food stored in the storage room and air inside the storage room may be sterilized effectively. Also, the storage room may be maintained clean.

Further, according to the refrigerator relating to at least one embodiment, the plurality of the storage rooms may be maintained clean by the sterilization passage independently separated from the cold air passage.

Still further, according to the refrigerator relating to at least one embodiment, the storage room may be sterilized and deodorized. In addition, remains of dead bacteria may be self-discomposed.

Still further according to the refrigerator relating to at least one embodiment, allergens that are allergy generation factors may be removed from the inside of the storage room. Because of this, the storage room may be managed more sanitarily and freshness of the stored food may be kept.

Still further, according to the refrigerator relating to at least one embodiment, the sterilization may be selectively performed based on the food introduction, the internal temperature change or the usage. Because of this, power consumption may be reduced.

Still further, according to the refrigerator relating to at least one embodiment, a kinds and amount or the smell factor of bacteria located in the storage room may be detected and the detected information may be displayed to the user.

Still further, according to the refrigerator relating to at least one embodiment, image information relating to shape or temperature distribution of specific food may be acquired and freshness of the food may be figured out, to display the freshness of the food to the user.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A refrigerator, comprising:
   a cabinet having at least one storage compartment;
   at least one door that selectively opens and closes the cabinet and the at least one storage compartment;
   plurality of shelves vertically disposed within the at least one storage compartment, that partitions the at bast one storage compartment into a plurality of storage sections;
   a first duct mounted on a rear wall of the at least one storage compartment to supply cold air, the first duct extending between the plurality of storage sections and having plurality of cold air supply holes that supplies the cold air into the plurality of storage sections;
   a filter module that filters air inside of the at least one storage compartment, the filter module comprising:
     a filter mounted on the rear wall of the at least one storage compartment to filter air within the at least one storage compartment;
     a second duct connected to toe niter, wherein the second duct supplies air filtered by the filter to the at least one storage compartment, extends between the plurality of storage sections, and includes a plurality of passing holes through which the filtered air is supplied into the plurality of storage sections; and
     a fan that allows air within the storage compartment to flow into the second duct through the filter,
   wherein air flow through the second duct does not cross with air flow through the first duct.

2. The refrigerator of claim 1, wherein the filter module further comprises a housing, and wherein the filter and the fan are disposed within the housing.

3. The refrigerator of claim 2, wherein the filter is removably disposed within the housing.

4. The refrigerator of claim 1, wherein the first and second ducts are integrated as a multi-duct adjacent the at least one storage compartment.

5. The refrigerator of claim 1, wherein the at least one first duct comprises at least two first ducts, and the second duct is positioned between the at least two first ducts.

6. The refrigerator of claim 1, wherein the filter comprises at least one sterilization device.

7. The refrigerator of claim 6, wherein the at least one sterilization device comprises at least one sterilization filter.

8. The refrigerator of claim 7, wherein the at least one sterilization filter is coated with a leuconostoc enzyme.

9. The refrigerator of claim 7, wherein the filter further comprises an anti-allergen filter.

10. The refrigerator of claim 9, wherein the filter farther comprises a deodorization filter.

11. The refrigerator of claim 1, wherein the module further comprises a housing, and wherein the filter and the fan are disposed within the housing.

12. The refrigerator of claim 11, wherein the filter is removably disposed within the housing.

13. The refrigerator of claim 6, wherein the at least one sterilization device comprises a UV light source.

14. The refrigerator of claim 13, wherein the UV light source is disposed within the second duct.

15. The refrigerator of claim 13, wherein the UV light source comprises a UV LED.

16. The refrigerator of claim 13, wherein the filter further comprises a photocatalyst filter.

17. The refrigerator of claim 16, wherein the photocatalyst filter is coated with titanium.

18. The refrigerator of claim 6, wherein the at least one sterilization device comprises a UV LED.

19. The refrigerator of claim 18, wherein the LED is disposed within the second duct.

20. The refrigerator of claim 1, further comprising:
    a plurality of shelves disposed within the at least one storage compartment.

21. The refrigerator of claim 1, further comprising a controller that selectively drives the fan.

22. The refrigerator of claim 21, further comprising an input that receives input of an operational mode of the filter module.

23. The refrigerator of claim 21, further comprising a display that displays the operational mode of the filter module.

24. The refrigerator of claim 1, wherein the second duct extends vertically in the cabinet and the plurality of passing holes extends vertically along the second duct.

25. The refrigerator of claim 24, wherein the filter module further comprises a housing, and wherein the filter and the fan are, disposed within the housing.

26. The refrigerator of claim 25, wherein the filter is removably disposed within the housing.

27. The refrigerator of claim 24, wherein the filter comprises at least one sterilization filter.

28. The refrigerator of claim 24, wherein the at least one sterilization filter is coated with a leuconostoc enzyme.

29. The refrigerator of claim 28, wherein the filter further comprises an anti-allergen filter.

30. The refrigerator of claim 29, wherein the filter further comprises a deodorization filter.

31. The refrigerator of claim 24, wherein the filter comprises a UV light source.

32. The refrigerator of claim 31, wherein the light source comprises a UV LED.

33. The refrigerator of claim 31, wherein the filter further comprises a photocatalyst filter.

34. The refrigerator of claim 24, further comprising:
    a plurality of shelves disposed within the at least one storage compartment.

35. The refrigerator of claim 24, further comprising a controller that selectively drives the fan.

36. The refrigerator of claim 35, further comprising an input that receives input of an operational mode of the filter module.

37. The refrigerator of claim 36, farther comprising a display that displays the operational mode of the filter module.

38. The refrigerator of claim 1, further comprising:
    a sensor that senses a status of stored goods within the at least one storage compartment; and a controller that controls an operation of the filter module based on a detection result of the sensor.

39. The refrigerator of claim 38, wherein the filter module comprises:

at least one steam generator.

40. The refrigerator of claim 39, wherein the sensor comprises at least one of:

a bio-sensor that detects a specific bacteria contaminant;

a gas sensor that detects an offensive smell;

a weight sensor that measures a weight of stored goods; or a temperature sensor that senses a temperature of the at least one storage compartment.

41. The refrigerator of claim 40, wherein the sensor comprises a bio-sensor.

42. The refrigerator of claim 41, further comprising:

a microbial response viewer (MRV) system that manages microbes for each of a predetermined kind of stored goods.

43. The refrigerator of claim 42, wherein the controller controls a spraying time and a spraying temperature of the at least one steam generator based on a kind and amount of bacteria detected by the bio-sensor and MRV system.

44. The refrigerator of claim 38, further comprising a display that displays a contamination status of the at least one storage compartment.

45. The refrigerator of claim 38, wherein the controller comprises:

an input that receives input of control commands for the filter module from a user.

46. The refrigerator of claim 38, further comprising:

a camera that captures an image of stored goods in the at least one storage compartment.

47. The refrigerator of claim 46, wherein the controller determines a contamination status and spoiling of stored goods based on a comparison between an image of the stored goods previously captured by the camera and a currently captured image.

48. The refrigerator of claim 46, wherein the camera is capable of detecting at least one of surface temperature distribution, color, or shape of the stored goods.

* * * * *